(12) United States Patent
Samsoondar

(10) Patent No.: US 7,816,124 B2
(45) Date of Patent: *Oct. 19, 2010

(54) DIAGNOSTIC WHOLE BLOOD AND PLASMA APPARATUS

(75) Inventor: James Samsoondar, Markham (CA)

(73) Assignee: Chromedx Inc., Markham, Ontario (CA)

( * ) Notice: Subject to any disclaimer, the term of this patent is extended or adjusted under 35 U.S.C. 154(b) by 376 days.

This patent is subject to a terminal disclaimer.

(21) Appl. No.: 11/432,616

(22) Filed: May 12, 2006

(65) Prior Publication Data

US 2006/0254962 A1  Nov. 16, 2006

(51) Int. Cl.
C12M 1/34 (2006.01)

(52) U.S. Cl. .................................. 435/287.3

(58) Field of Classification Search ....................... None
See application file for complete search history.

(56) References Cited

U.S. PATENT DOCUMENTS

| | | | |
|---|---|---|---|
| 3,874,850 A | 4/1975 | Sorensen et al. | |
| 4,013,417 A | 3/1977 | Raffaele | |
| 4,088,448 A | 5/1978 | Lilja et al. | |
| 4,409,106 A * | 10/1983 | Furuta et al. | 210/732 |
| 4,613,422 A | 9/1986 | Lauks et al. | |
| 4,668,399 A * | 5/1987 | Duggins | 210/637 |
| 4,695,274 A | 9/1987 | Fox | |
| 4,756,884 A | 7/1988 | Hillman et al. | |
| 4,849,340 A * | 7/1989 | Oberhardt | 435/13 |
| 4,900,310 A | 2/1990 | Ogle, II | |
| 5,096,669 A | 3/1992 | Lauks et al. | |
| 5,112,455 A | 5/1992 | Cozzette et al. | |
| 5,430,542 A | 7/1995 | Shepherd | |
| 5,638,828 A | 6/1997 | Lauks et al. | |
| 5,725,574 A * | 3/1998 | Nguyen | 623/6.54 |
| 5,725,774 A * | 3/1998 | Neyer | 210/645 |
| 5,957,579 A | 9/1999 | Kopf-Sill et al. | |
| 5,976,433 A * | 11/1999 | Komatsu et al. | 264/41 |
| 6,066,243 A | 5/2000 | Anderson et al. | |
| 6,130,098 A | 10/2000 | Handique et al. | |
| 6,143,247 A * | 11/2000 | Sheppard et al. | 422/63 |
| 6,155,991 A | 12/2000 | Beat et al. | |
| 6,262,798 B1 | 7/2001 | Shepard et al. | |
| 6,348,156 B1 * | 2/2002 | Vishnoi et al. | 210/739 |
| 6,581,441 B1 | 6/2003 | Paul | |
| 6,597,438 B1 * | 7/2003 | Cabuz et al. | 356/39 |
| 6,695,147 B1 | 2/2004 | Yager et al. | |
| 6,787,368 B1 | 9/2004 | Wong et al. | |
| 6,878,271 B2 | 4/2005 | Gilbert | |
| 6,962,823 B2 * | 11/2005 | Empedocles et al. | 438/3 |
| 6,966,880 B2 * | 11/2005 | Boecker et al. | 600/583 |
| 7,018,838 B2 | 3/2006 | Murphy et al. | |
| 7,094,345 B2 * | 8/2006 | Gilbert et al. | 210/321.61 |
| 7,258,774 B2 | 8/2007 | Chou et al. | |
| 7,314,718 B1 * | 1/2008 | Dasgupta et al. | 435/7.1 |
| 7,682,833 B2 * | 3/2010 | Miller et al. | 436/165 |
| 2002/0025576 A1 | 2/2002 | Northrup et al. | |
| 2002/0045272 A1 | 4/2002 | McDevitt et al. | |
| 2002/0091057 A1 * | 7/2002 | Westberg et al. | 494/45 |
| 2002/0100714 A1 | 8/2002 | Staats | |
| 2002/0106786 A1 | 8/2002 | Carvalho et al. | |
| 2002/0142471 A1 | 10/2002 | Handique et al. | |
| 2002/0143437 A1 | 10/2002 | Handique et al. | |
| 2002/0164824 A1 | 11/2002 | Xiao et al. | |
| 2002/0177135 A1 | 11/2002 | Doung et al. | |
| 2002/0187072 A1 | 12/2002 | Karp | |
| 2002/0187074 A1 | 12/2002 | O'Connor et al. | |
| 2002/0197167 A1 * | 12/2002 | Kornelsen | 417/53 |
| 2003/0049862 A1 | 3/2003 | He et al. | |
| 2003/0123047 A1 | 7/2003 | Pettersen et al. | |
| 2003/0175990 A1 | 9/2003 | Hayenga et al. | |
| 2003/0209451 A1 | 11/2003 | Dineen et al. | |
| 2003/0215855 A1 | 11/2003 | Dubrow et al. | |
| 2004/0089616 A1 | 5/2004 | Kellogg et al. | |
| 2004/0176704 A1 | 9/2004 | Stevens et al. | |

(Continued)

FOREIGN PATENT DOCUMENTS

JP  60-011166 A  1/1985

OTHER PUBLICATIONS

Office Action issued in connection with co-pending U.S. Appl. No. 11/108,912, filed Apr. 19, 2005 (retrievable from PAIR), mailed on Jul. 10, 2008.

(Continued)

Primary Examiner—Ann Y Lam
(74) Attorney, Agent, or Firm—Ian C. McMillan; Bereskin & Parr LLP/S.E.N.C.R.L., s.r.l.

(57) ABSTRACT

An apparatus suitable for measuring at least one plasma analyte in plasma extracted from a whole blood sample within the apparatus is provided. The apparatus can be adapted for insertion into a slot in a meter, which can preferably perform at least spectroscopic or biosensor measurement. The apparatus comprises a whole blood flow path, which begins at the inlet opening of the apparatus, and terminates at a vent or a suction chamber. Included in the blood flow path is a flow-through filtration chamber. The filtration chamber comprises at least one membrane separating a blood compartment from a plasma compartment. The apparatus further comprises a plasma flow path, which begins at the plasma compartment and terminates at a vent or a suction chamber. The plasma flow path includes a plasma analyte signal providing means. The signal is transmitted to a processor in the meter for preparing analyte measurements.

20 Claims, 17 Drawing Sheets

U.S. PATENT DOCUMENTS

| | | | |
|---|---|---|---|
| 2004/0176705 A1 | 9/2004 | Stevens et al. | |
| 2004/0189311 A1 | 9/2004 | Glezer et al. | |
| 2004/0224362 A1 | 11/2004 | Gjerde et al. | |
| 2004/0254419 A1 | 12/2004 | Wang et al. | |
| 2005/0026273 A1 | 2/2005 | Zarur et al. | |
| 2005/0130226 A1 | 6/2005 | Ahn et al. | |
| 2005/0130292 A1 | 6/2005 | Ahn et al. | |
| 2005/0152808 A1 | 7/2005 | Ganesan | |
| 2005/0153434 A1 | 7/2005 | Andersson et al. | |
| 2005/0233352 A1* | 10/2005 | Zoval | 435/6 |
| 2006/0257941 A1 | 11/2006 | McDevitt et al. | |
| 2007/0052956 A1 | 3/2007 | Blair | |
| 2007/0150223 A1 | 6/2007 | Abraham-Fuchs et al. | |

OTHER PUBLICATIONS

Office Action issued in connection with co-pending U.S. Appl. No. 11/103,619, filed Apr. 12, 2005 (retrievable from PAIR), mailed on Jun. 25, 2008.

Office Action issued in connection with co-pending U.S. Appl. No. 11/415,284, filed May 2, 2006 (retrievable from PAIR), mailed on Aug. 5, 2008.

Co-pending U.S. Appl. No. 11/466,588, "Hollow Needle Assembly", filed Aug. 23, 2006. (Retrievable from PAIR).

Co-pending U.S. Appl. No. 11/738,889, "Hollow Needle Assembly" (CIP), filed Apr. 23, 2007. (Retrievable from PAIR).

Co-pending U.S. Appl. No. 11/835,631, "Plasma Extraction Apparatus" (CIP), filed Aug. 8, 2007. (Retrievable from PAIR).

Co-pending U.S. Appl. No. 12/016,315, "Spectroscopic Sample Holder" CIP, filed Jan. 18, 2008. (Retrievable from PAIR).

Co-pending U.S. Appl. No. 11/108,912, "Joint-Diagnostic Spectroscopic and Biosensor Cartridge", filed Apr. 19, 2005. (Retrievable from PAIR).

Co-pending U.S. Appl. No. 11/415,284, "Joint-Diagnostic Spectroscopic and Biosensor Meter" CIP, filed May 2, 2006. (Retrievable from PAIR).

Co-pending U.S. Appl. No. 11/103,619, "Blood Collection and Measurement Apparatus", Apr. 12, 2005. (Retrievable from PAIR).

Office Action issued in connection with co-pending U.S. Appl. No. 11/103,619, filed Apr. 12, 2005, mailed on Jan. 5, 2009 (retrievable from Pair).

Office Action issued in connection with co-pending U.S. Appl. No. 11/415,284, filed May 2, 2006, mailed on Jan. 23, 2009 (retrievable from Pair).

Office Action issued in connection with co-pending U.S. Appl. No. 11/466,588, filed Aug. 23, 2006, mailed on Feb. 20, 2009 (retrievable from Pair).

Office Action issued in connection with co-pending U.S. Appl. No. 11/835,631, filed Aug. 8, 2007 (retrievable from Pair), mailed on Oct. 6, 2008.

Response filed in connection with co-pending U.S. Appl. No. 11/103,619, filed Apr. 12, 2005 (retrievable from Pair).

Office Action issued in connection with co-pending U.S. Appl. No. 12/016,315, filed Jan. 18, 2008 (retrievable from Pair), mailed on Oct. 20, 2008.

Office Action issued in connection with co-pending U.S. Appl. No. 12/016,315, filed Jan. 18, 2008 (retrievable from PAIR), mailed on Apr. 2, 2009.

Office Action issued in connection with co-pending U.S. Appl. No. 12/016,315 (retrievable from Pair), mailed Sep. 24, 2009.

Office Action issued in connection with co-pending U.S. Appl. No. 12/016,315, filed Jan. 18, 2008, mailed on Sep. 24, 2009.

Office Action issued in connection with co-pending U.S. Appl. No. 11/415,284, filed May 2, 2006, mailed on Nov. 25, 2009.

Advisory Action received on co-pending U.S. Appl. No. 11/416,284, filed on Aug. 2, 2006, mailed on Feb. 22, 2010.

Office Action issued in connection with co-pending U.S. Appl. No. 11/835,631 filed on Aug. 8, 2007, mailed on Mar. 25, 2010.

Office Action issued in connection with co-pending U.S. Appl. No. 11/108,912, filed on Apr. 19, 2005, mailed on Jul. 10, 2008.

Office Action issued in connection with co-pending U.S. Appl. No. 11/415,284, filed on May 2, 2006, mailed on Nov. 25, 2009.

Office action issued in connection with co-pending U.S. Appl. No. 11/103,619 filed on Apr. 12, 2005, mailed on Jan. 5, 2009.

Office action issued in connection with co-pending U.S. Appl. No. 11/415,284, filed on May 12, 2006, mailed on Aug. 5, 2008.

Waters Medical Systems, "Oximetry", retrieved from http://www.watersmed.com/oximetry.html, dated Sep. 30, 2004.

Office Action issued in connection with co-pending U.S. Appl. No. 11/835,631 filed on Aug. 8, 2007, mailed on Jun. 19, 2009.

Advisory Office Action issued in connection with co-pending U.S. Appl. No. 12/016,315 filed on Jan. 18, 2008, mailed on Jun. 26, 2009.

Restriction Requirement Office Action issued in Connection with co-pending U.S. Appl. No. 11/466,588 filed on Aug. 23, 2006, mailed on Feb. 20, 2009.

K. A. Erickson and P. Wilding, Clinical Chemistry 39(2): 283-287, 1993.

Restriction Requirement Office Action received in connection with co-pending U.S. Appl. No. 11/738,889 filed on Apr. 23, 2007, mailed on May 26, 2010.

Notice of Allowance Office Action issued in connection with co-pending U.S. Appl. No. 12/016,315, filed on Jan. 1, 2008, mailed on Mar. 26, 2010.

Office Action issued in connection with co-pending U.S. Appl. No. 11/415,284, filed on May 2, 2006, mailed on Apr. 13, 2010.

Co-pending U.S. Appl. No. 12/752,048, "Blood Sample Holder for Spectroscopic Analysis", filed Mar. 31, 2010.

Notice of Allowance issued in connection with co-pending U.S. Appl. No. 11/835,631, filed on Aug. 8, 2007, mailed on Jul. 1, 2010.

* cited by examiner

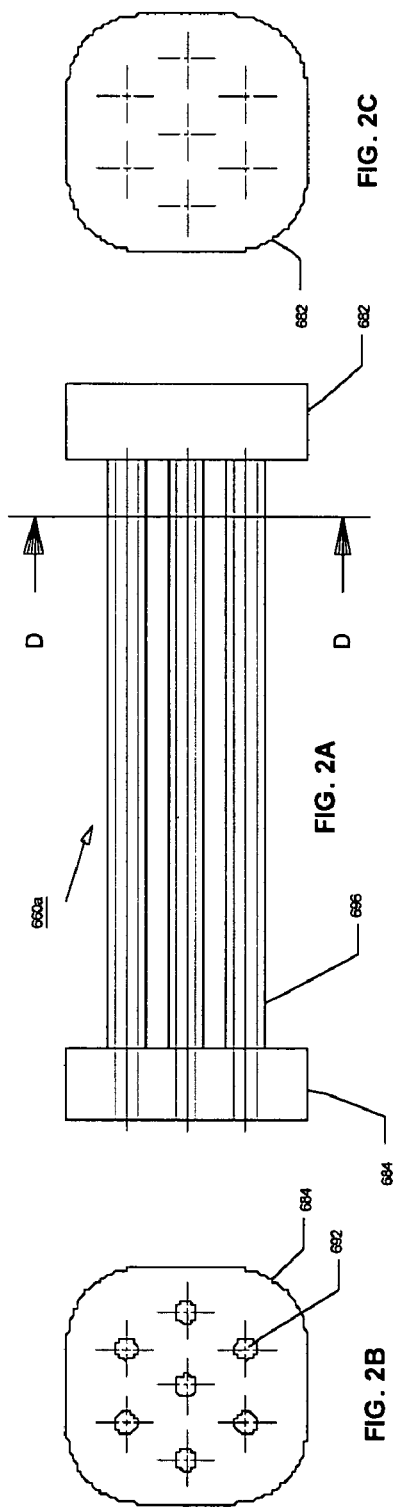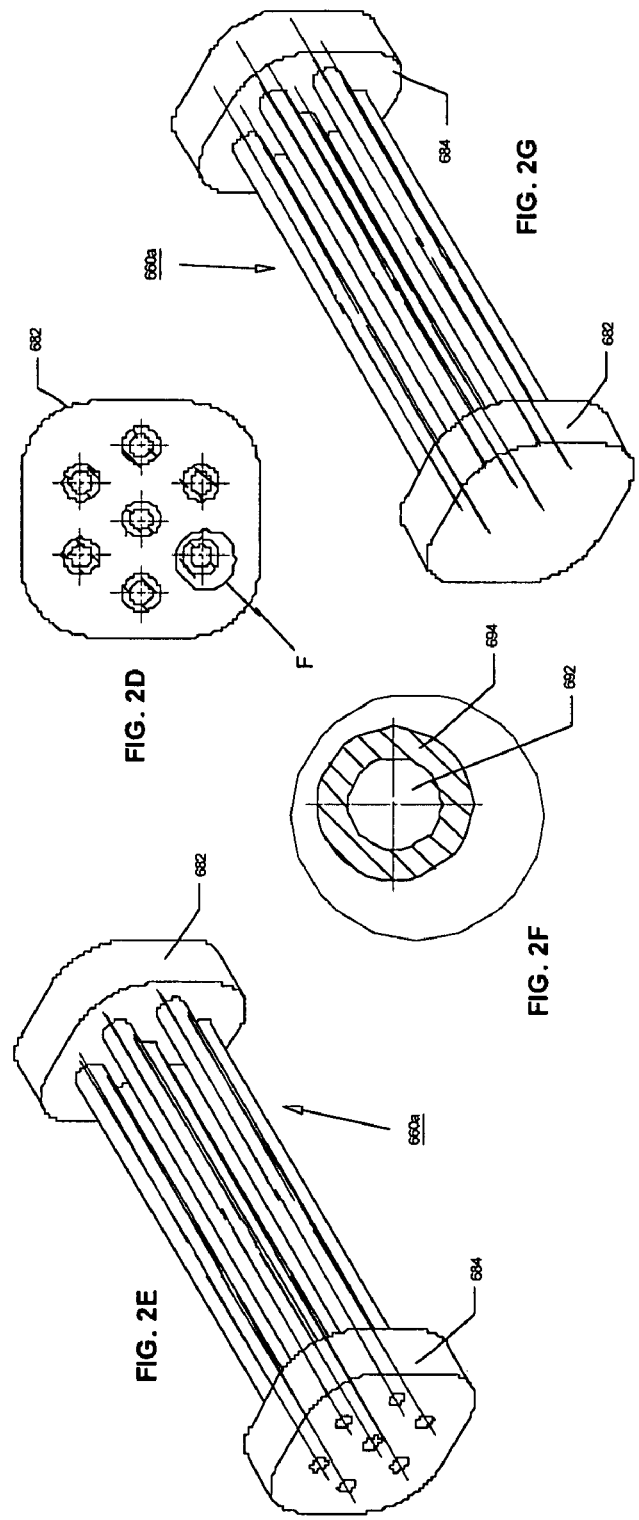

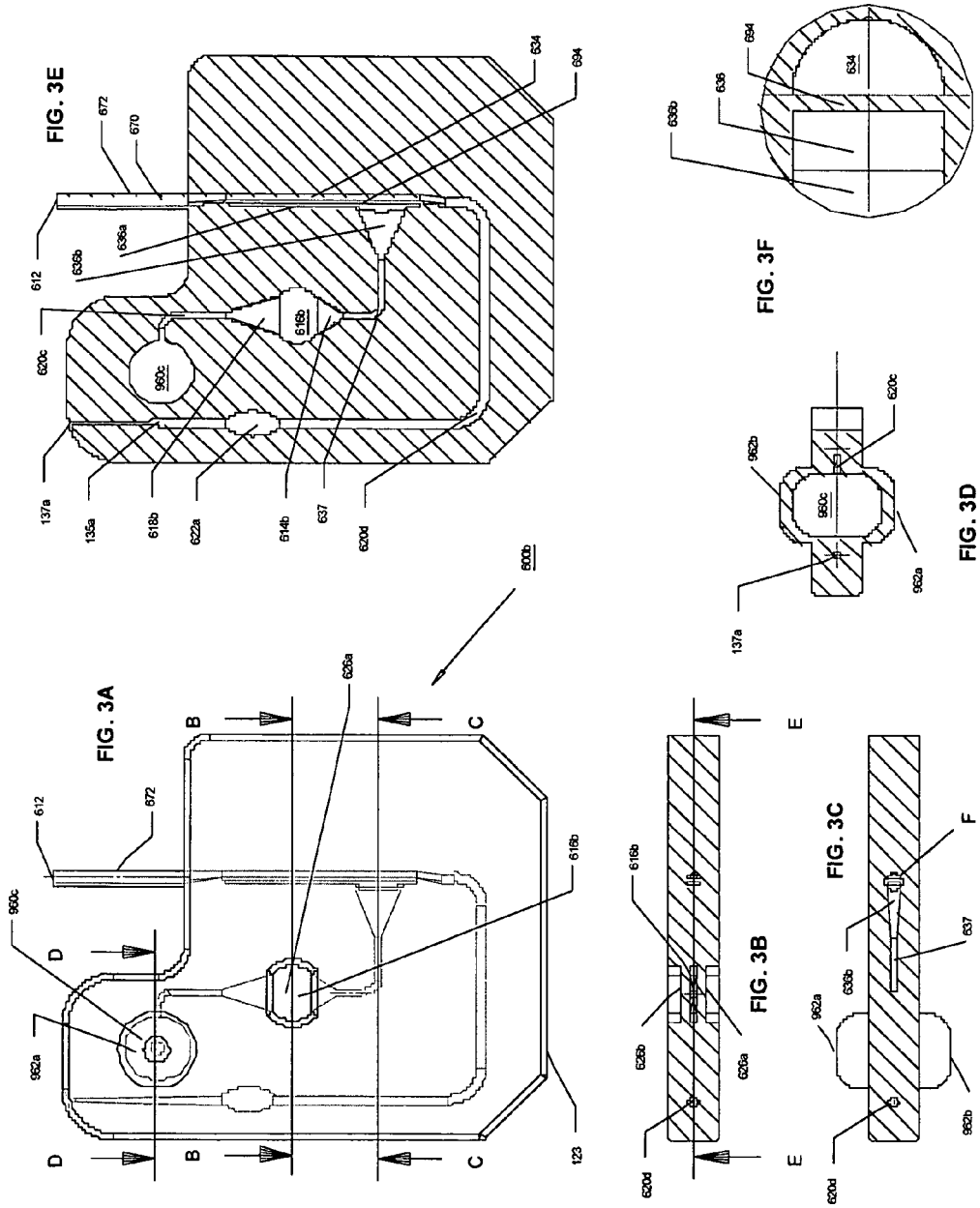

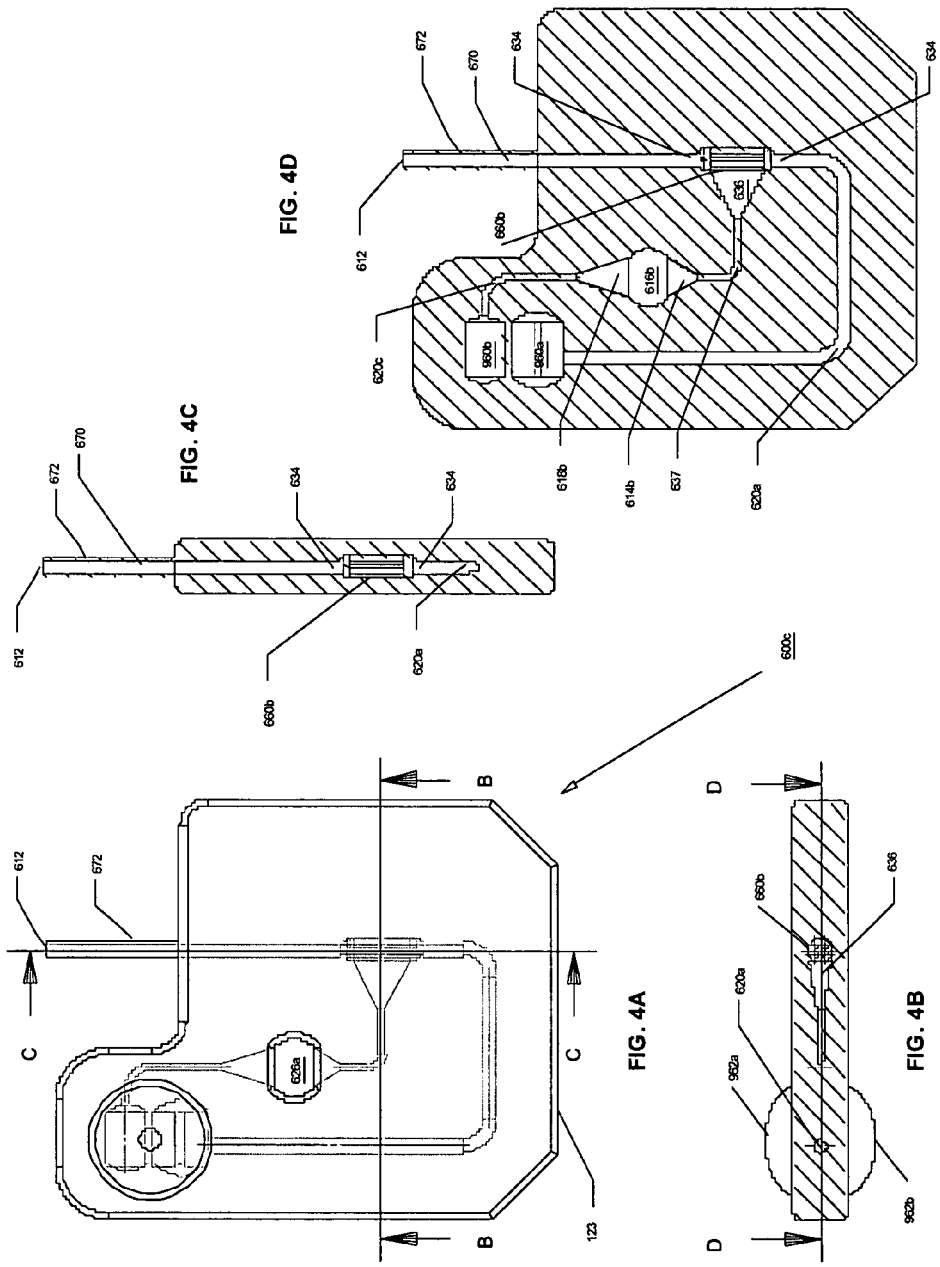

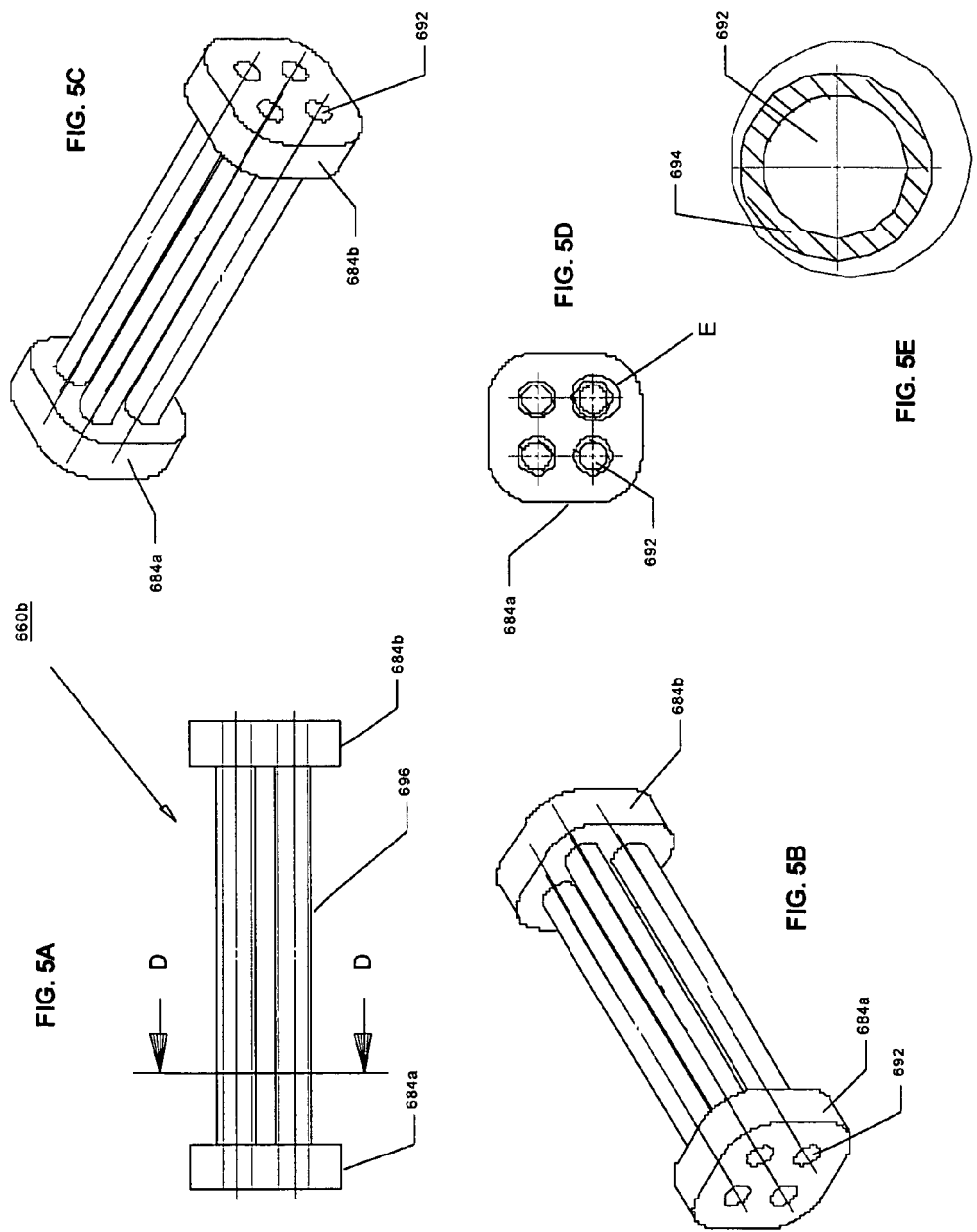

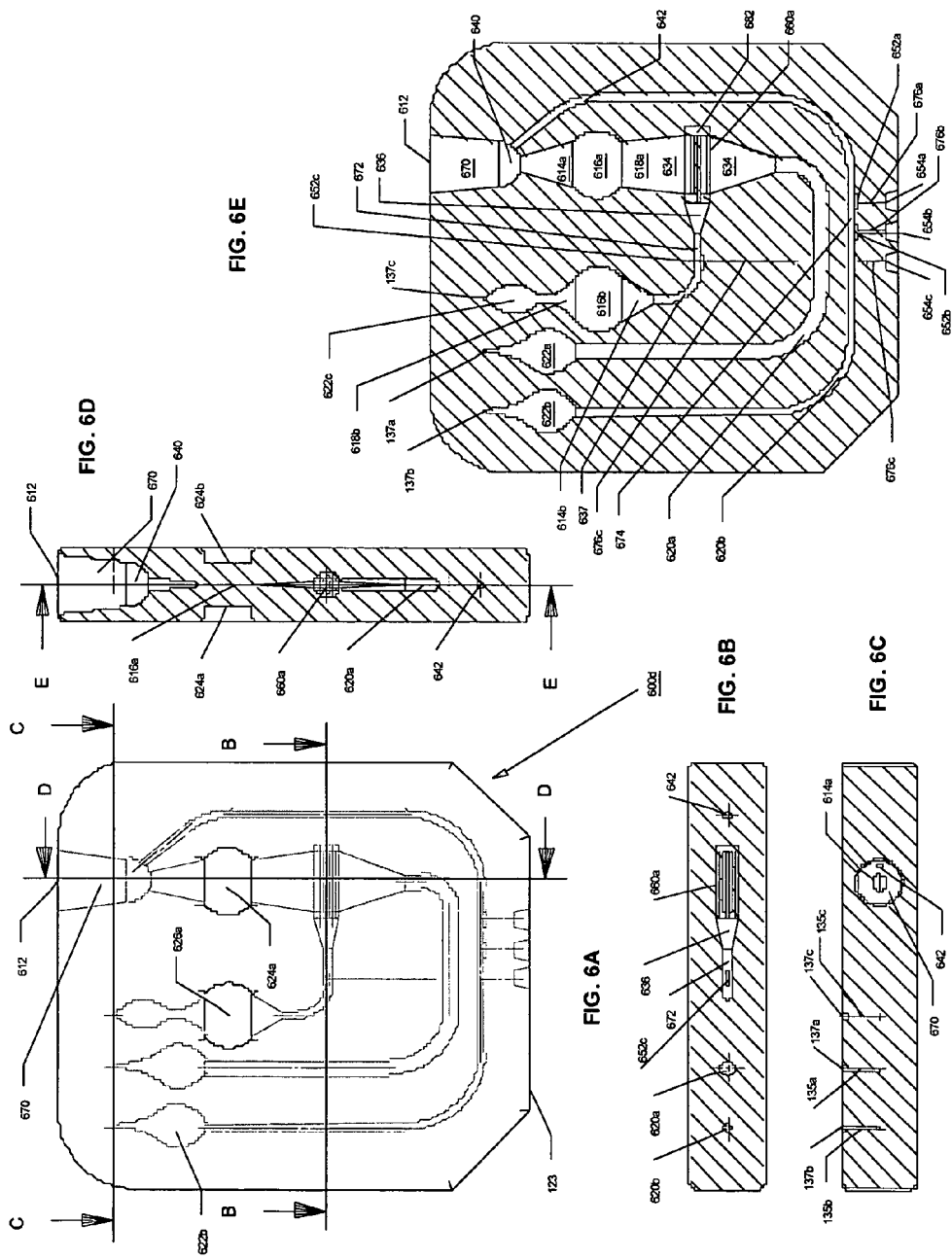

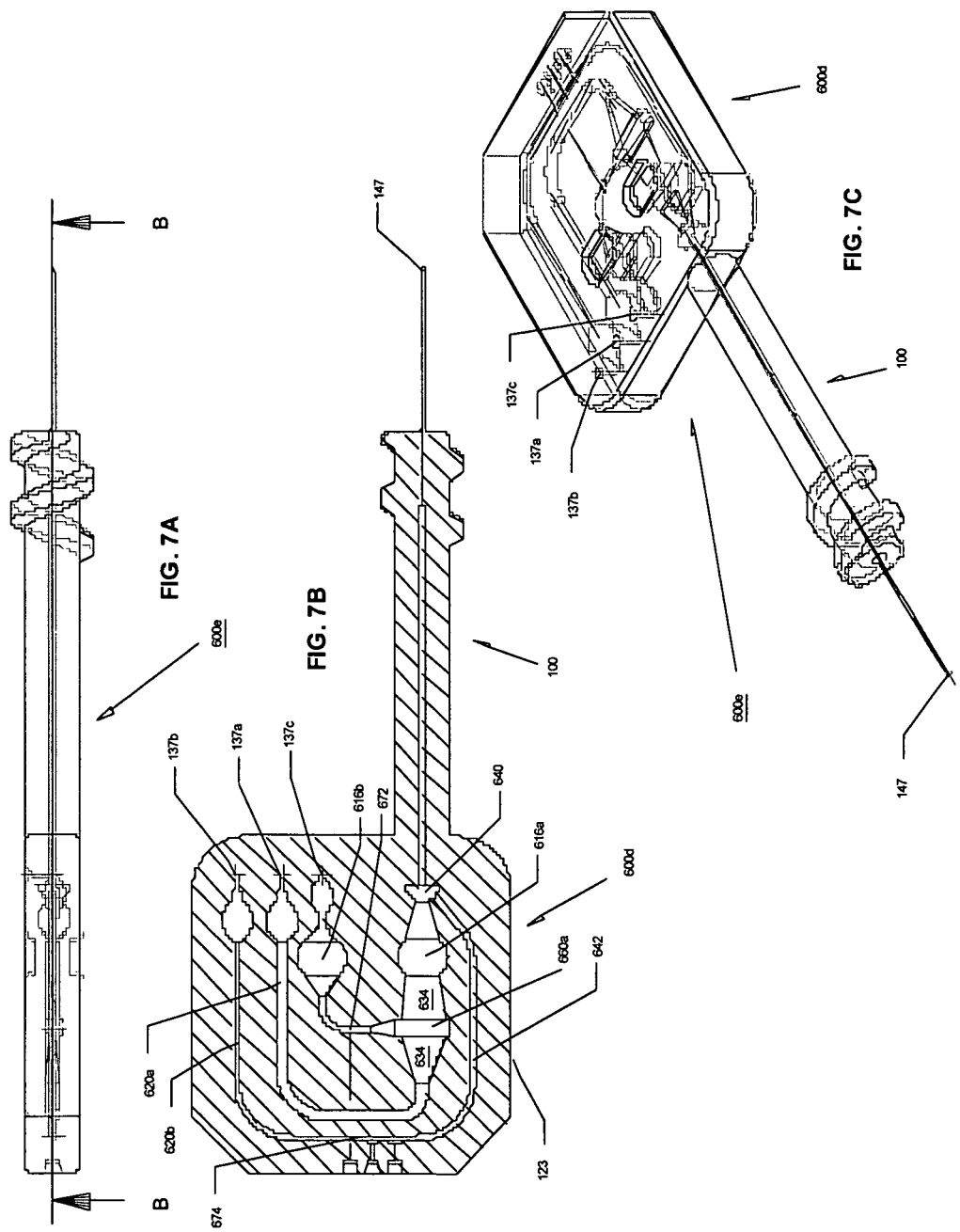

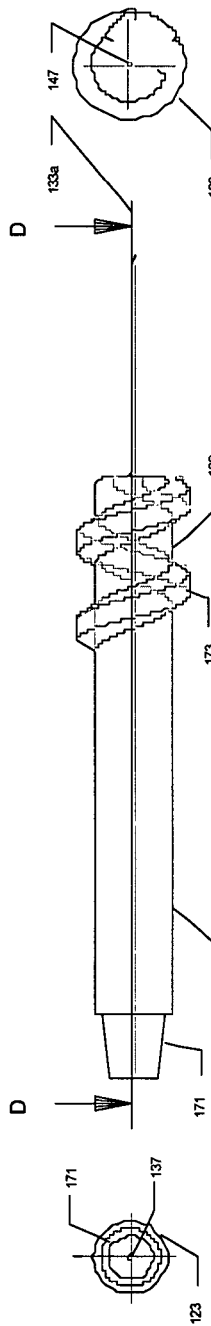
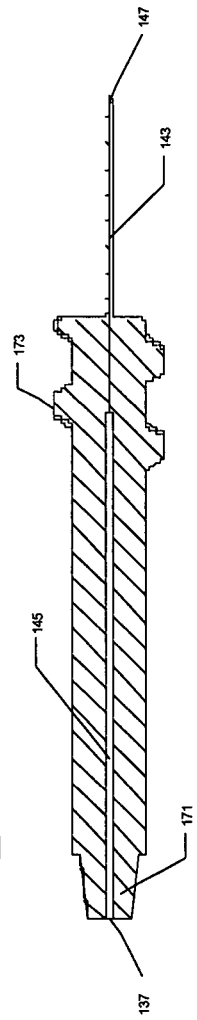
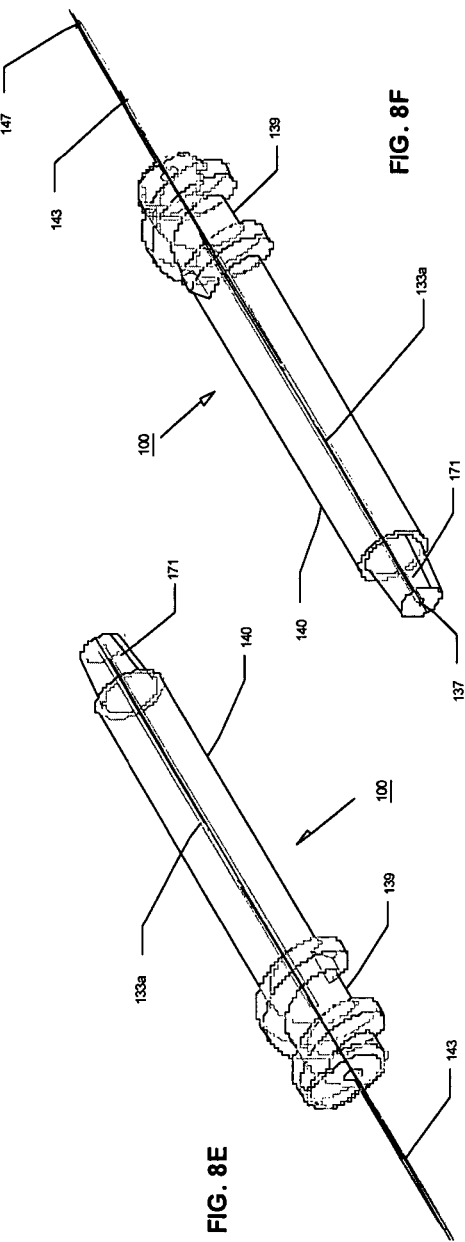

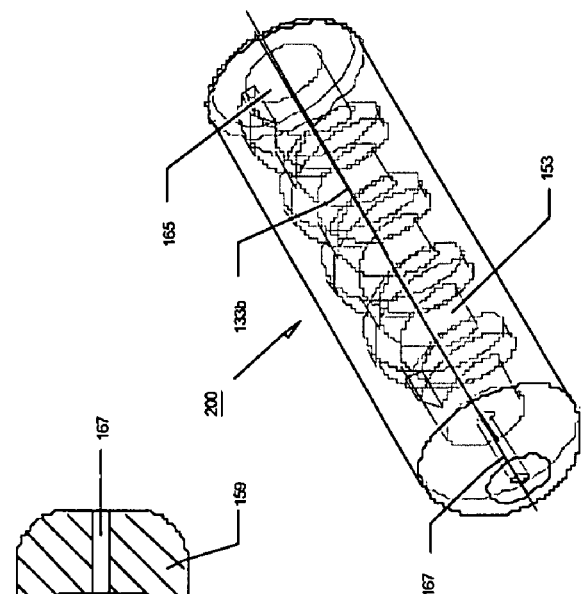
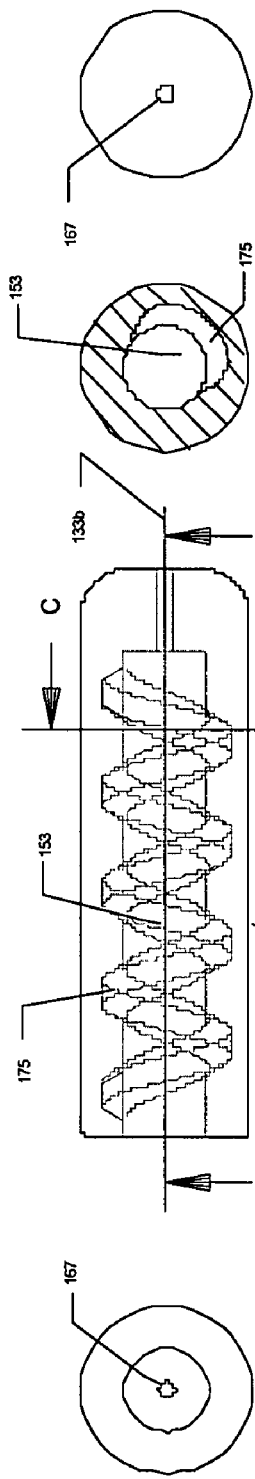
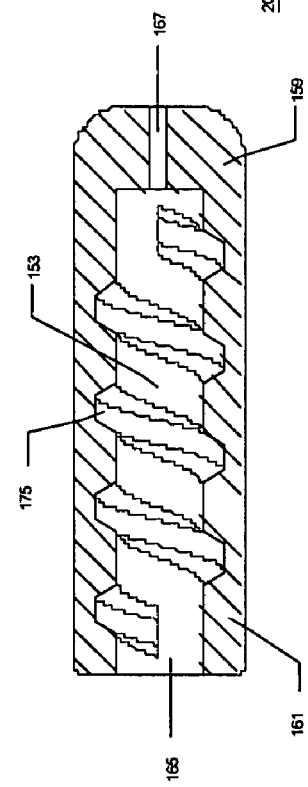
FIG. 9D
FIG. 9C
FIG. 9F
FIG. 9A
FIG. 9E
FIG. 9B

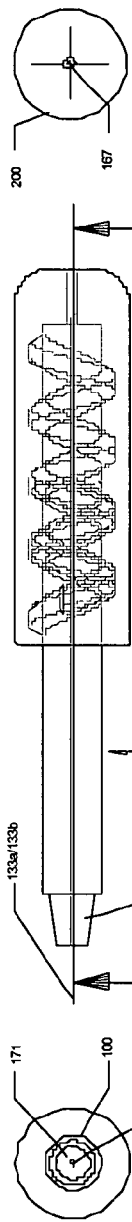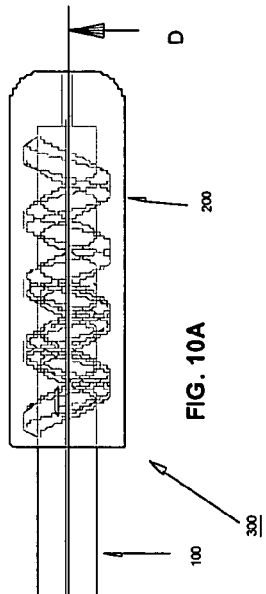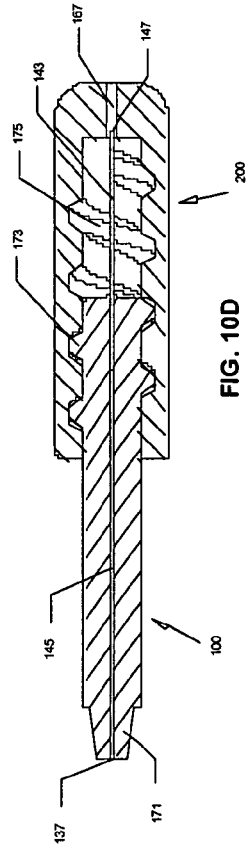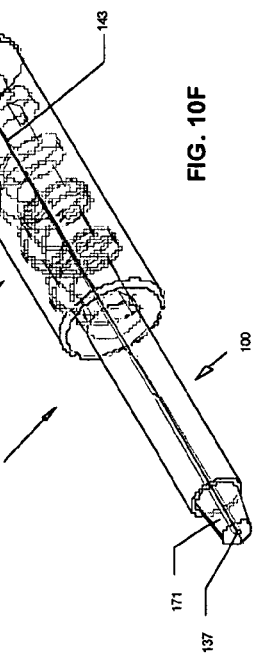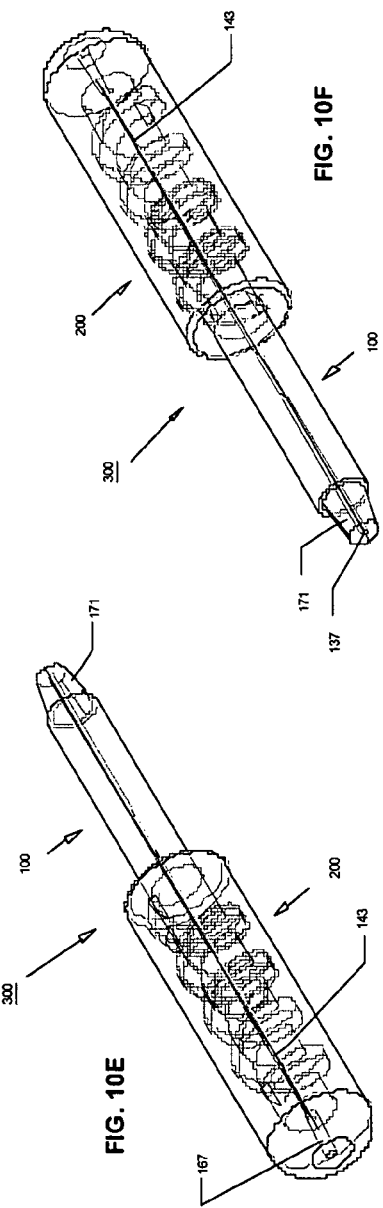

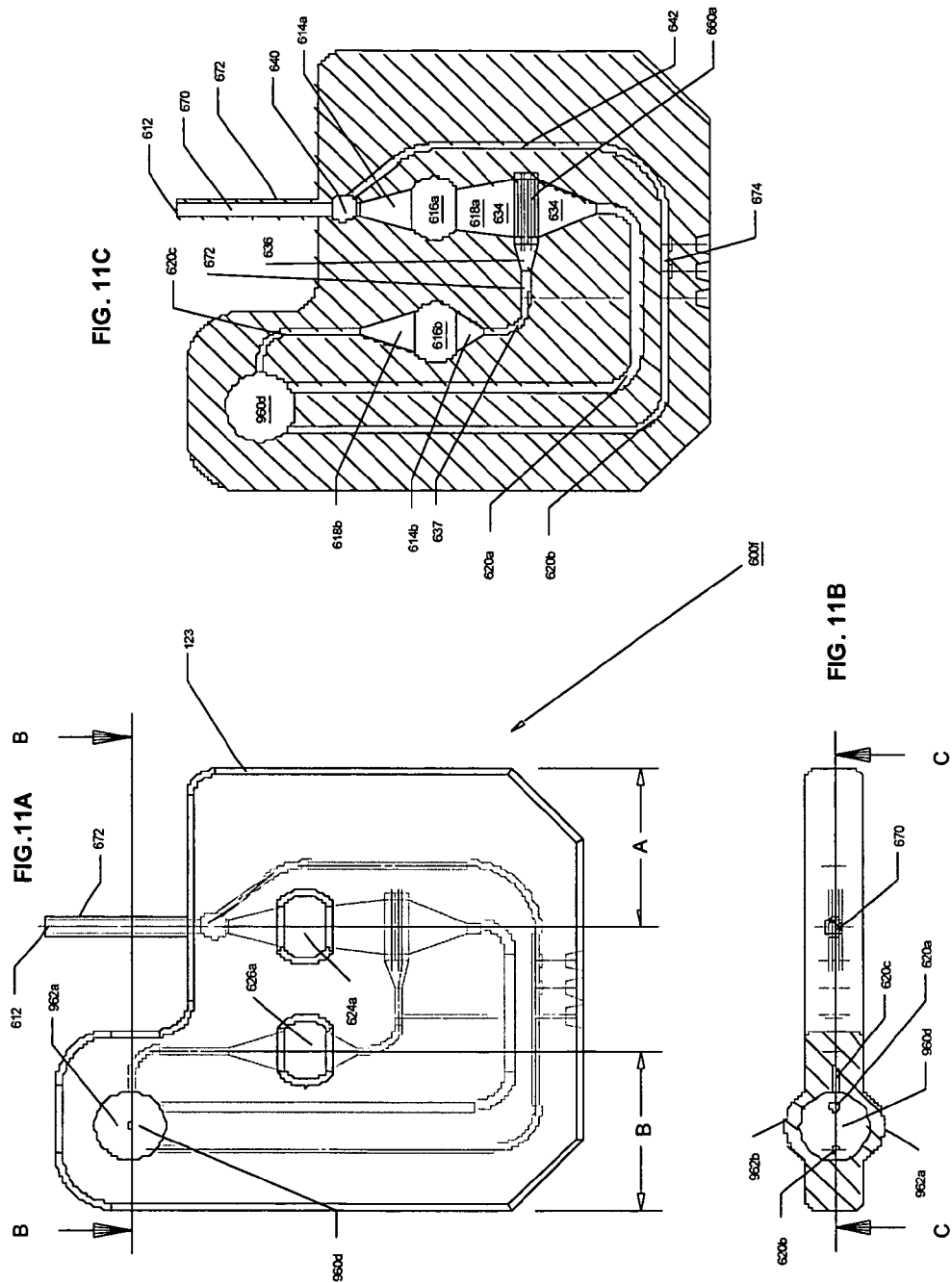

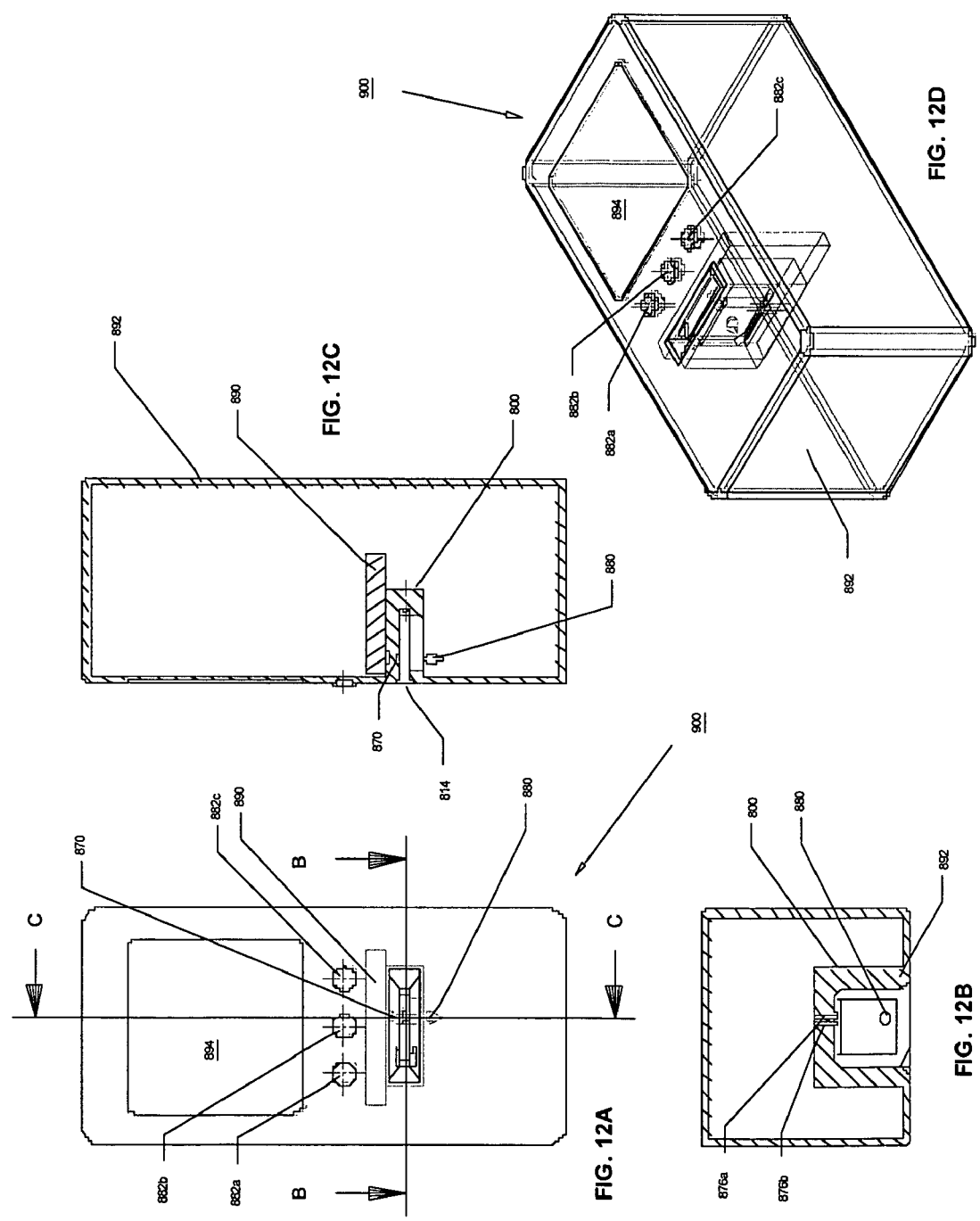

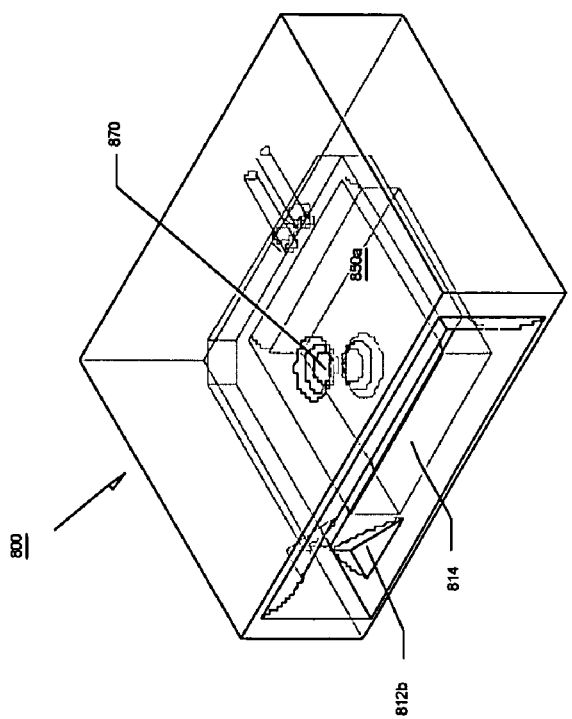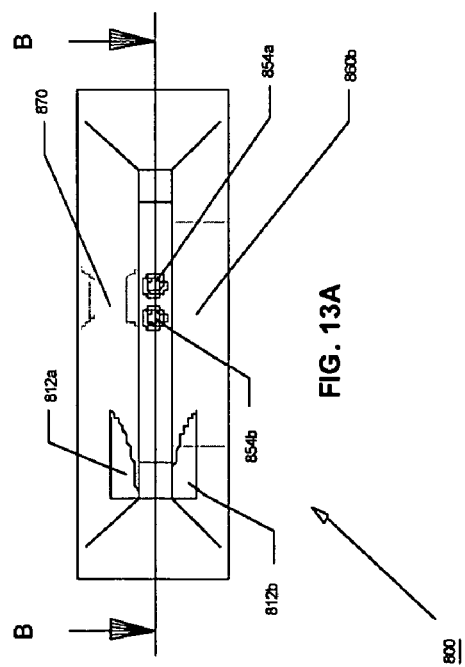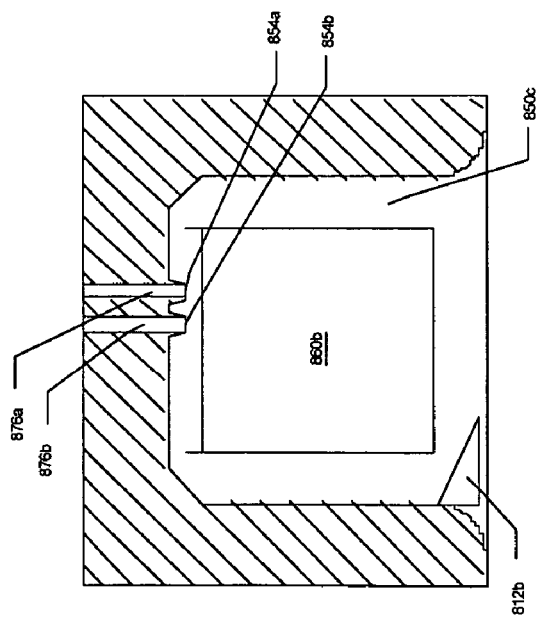

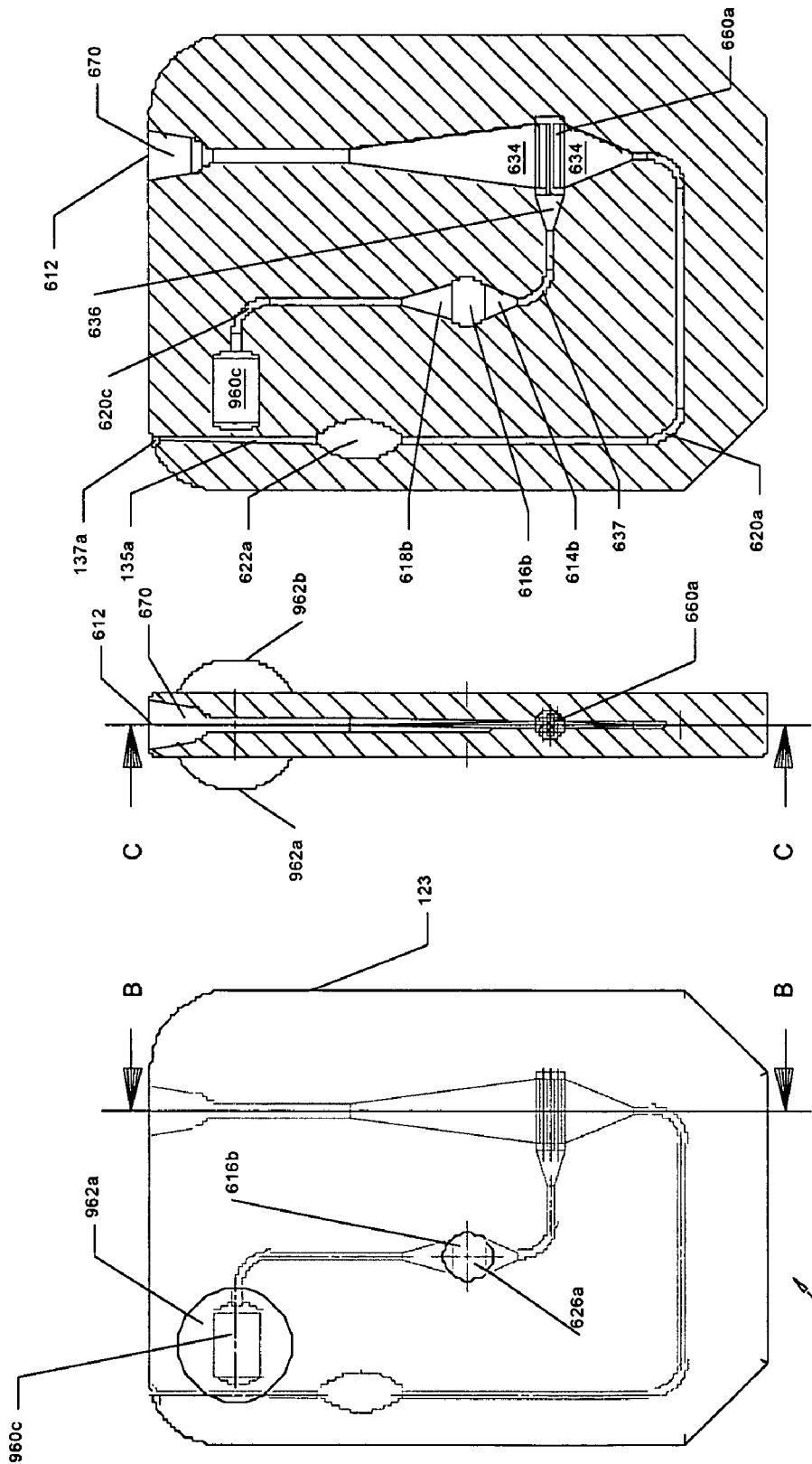

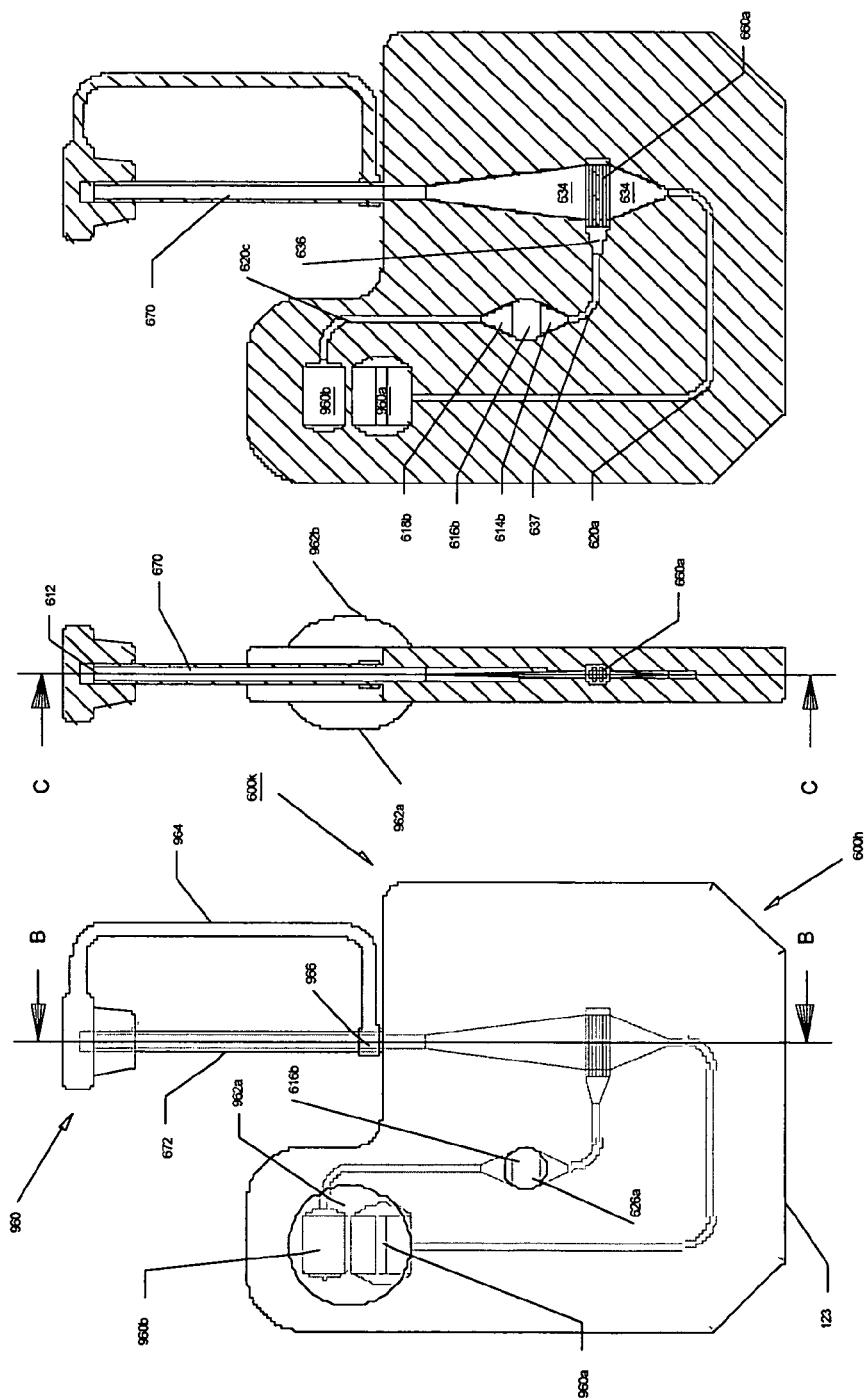

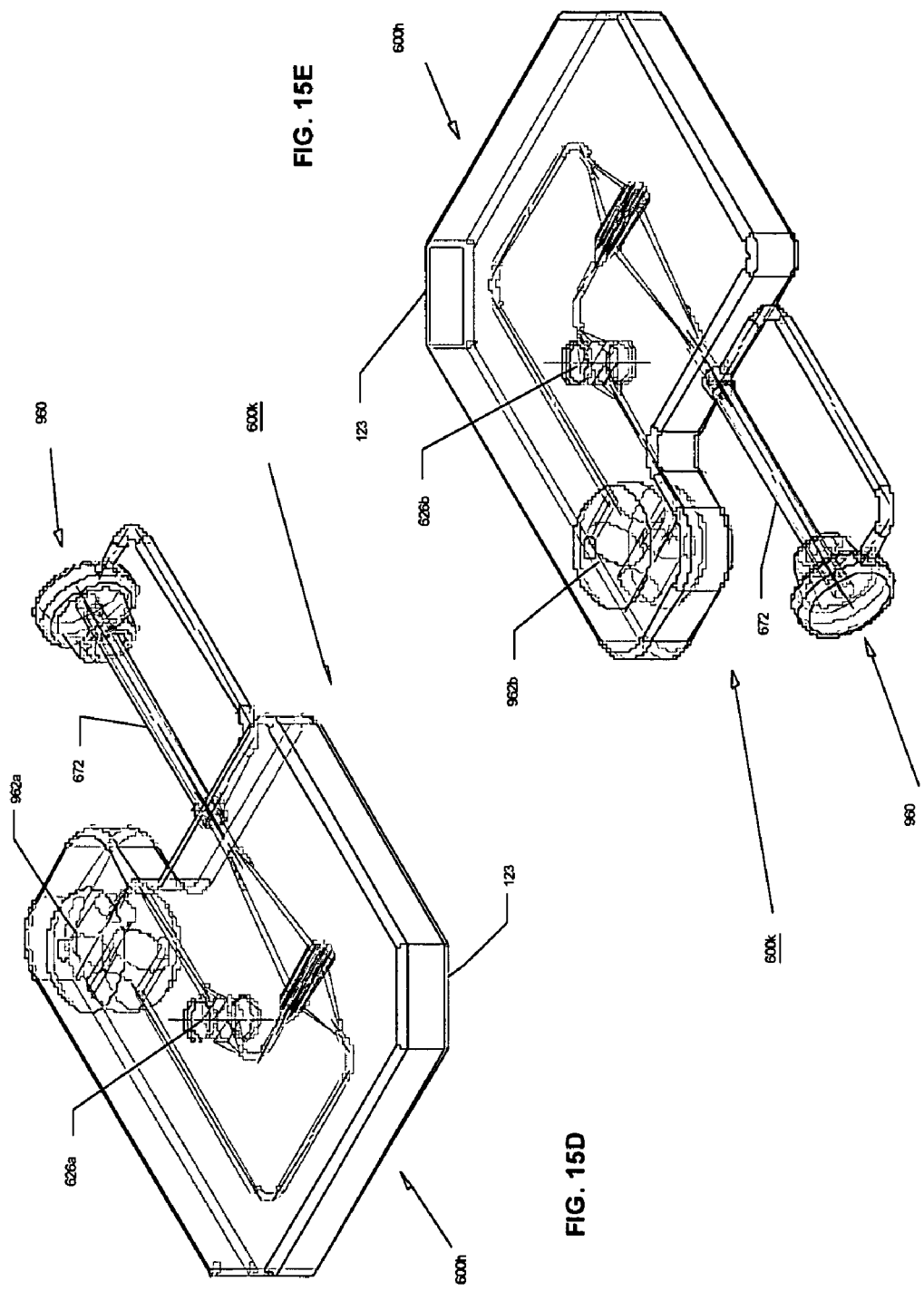

DIAGNOSTIC WHOLE BLOOD AND PLASMA APPARATUS

FIELD OF THE INVENTION

The invention relates to an apparatus that separates plasma from whole blood within the apparatus, for measurement of analytes in the plasma.

BACKGROUND OF THE INVENTION

Many medical diagnostic tests are performed in a medical laboratory, on serum and plasma. Serum is the yellow liquid obtained from "whole blood" (also referred to as blood) after the blood is allowed to clot, and the clot is removed by centrifugation; plasma is the yellow liquid obtained from blood by centrifugation of blood before the blood is allowed to clot, and the packed red cells are removed by centrifugation. Plasma is usually obtained by adding an anticoagulant like heparin to the blood, to prevent clotting.

Spectroscopy or spectroscopic methods, with and without reagents added to the sample, are common methods used to measure analytes in serum and plasma. In spectroscopic measurements, the hemoglobin inside the red cells absorbs a very significant portion of the incident or illuminating electromagnetic radiation (EMR), and the red cells cause significant attenuation of the incident EMR due to scattering of EMR away from the photodetector. Therefore, when one is interested in the plasma concentration of an analyte, the serum or plasma is preferred. As an example, bilirubin measurement by spectroscopy is accomplished much easier in serum and plasma than in whole blood. On the other hand, certain analytes can only be measured in blood because they only exist within the red cells, for example the various hemoglobin species.

Currently, not all diagnostic tests can be performed by spectroscopic methods, and the use of biosensors is another example of measurement techniques that can assist in expanding the menu of diagnostic tests. Because serum and plasma are less viscous that blood, serum or plasma may be preferred to blood when certain biosensors are employed.

Another reason for preferring serum and plasma over whole blood, is the ability to detect hemolysis, turbidity, and elevated bilirubin in the serum and plasma, which cannot be detected in whole blood, and which affect the accuracy of many analyte measurements. Hemolysis is the release of hemoglobin and other red cell contents into the plasma or serum after rupture of red blood cells, and turbidity is the presence of light-scattering particles, for example, fat particles in the blood.

In point-of-care testing or near patient testing, the preferred sample is whole blood because the time and cost required for clotting and/or centrifugation is eliminated, and less blood is required. A drop of blood from a pin prick is the sample of choice for point-of-care testing or measuring devices. However, if plasma or serum were as readily available as a drop of blood, they would be preferred over whole blood for measurement of most analytes.

SUMMARY OF THE INVENTION

According to an aspect of an embodiment of the invention there is provided a disposable apparatus adapted for insertion into the slot of a meter for measuring at least one plasma analyte in plasma extracted from a blood sample within the apparatus, the apparatus comprising: (a) a housing; (b) an inlet opening in the housing for receiving the blood sample; (c) a first groove in the housing defining a blood flow path beginning at the inlet opening and terminating at a manually operable first compression suction chamber for facilitating blood flow in the blood flow path, wherein the first compression suction chamber comprises a first cavity within the housing, wherein a wall portion of the first cavity is defined by the housing; (d) a filtration chamber comprising a membrane separating a plasma compartment from the blood flow path, wherein the blood flow path fluidly intersects with the filtration chamber, and a blood flow direction defined by the blood flow path at the intersection with the filtration chamber is substantially parallel to a surface of the membrane; and (e) a second groove in the housing defining a plasma flow path beginning at the plasma compartment and terminating at a manually operable second compression suction chamber for pulling the plasma across the membrane from the blood flow path into the plasma flow path, wherein the second compression suction chamber comprises a second cavity within the housing, wherein a wall portion of the second cavity is defined by the housing, and wherein the plasma flow path comprises at least one of (i) an optical chamber defining a void for containing the plasma for analysis, wherein the optical chamber comprises at least one optical wall-portion to facilitate detection of an EMR-based signal derived from the plasma for measuring the at least one plasma analyte, and (ii) a plasma biosensor chamber comprising at least one biosensor for measuring the at least one plasma analyte, wherein the at least one biosensor is in electrical communication with an electrical output located on an external surface of the housing, the electrical output being operable to receive plasma biosensor data from the biosensor and to transmit the biosensor data to the meter when the apparatus is inserted in the slot.

According to another aspect of an embodiment of the invention there is provided a disposable apparatus adapted for insertion into the slot of a meter for measuring at least one plasma analyte in plasma extracted from a blood sample within the apparatus, the apparatus comprising: (a) a housing; (b) an inlet opening in the housing for receiving the blood sample; (c) a first groove in the housing defining a blood flow path beginning at the inlet opening and terminating at a vent for facilitating blood flow in the blood flow path; (d) a filtration chamber comprising a membrane separating a plasma compartment from the blood flow path, wherein the blood flow path fluidly intersects with the filtration chamber; and (e) a second groove in the housing defining a plasma flow path beginning at the plasma compartment and terminating at a manually operable compression suction chamber for pulling the plasma across the membrane from the blood flow path into the plasma flow path, wherein the manually operable compression suction chamber comprises a cavity within the housing, wherein a wall portion of the cavity is defined by the housing, and wherein the plasma flow path comprises at least one of (i) an optical chamber defining a void for containing the plasma for analysis, wherein the optical chamber comprises at least one optical wall-portion to facilitate detection of an EMR-based signal derived from the plasma for measuring the at least one plasma analyte, and (ii) a plasma biosensor chamber comprising at least one biosensor for measuring the at least one plasma analyte, wherein the at least one biosensor is in electrical communication with an electrical output located on an external surface of the housing, the electrical output being operable to receive plasma biosensor data from the biosensor and to transmit the biosensor data to the meter when the apparatus is inserted in the slot.

Other aspects and features of the present invention will become apparent, to those ordinarily skilled in the art, upon review of the following description of the specific embodiments of the invention.

BRIEF DESCRIPTION OF THE DRAWINGS

For a better understanding of the present invention, and to show more clearly how it may be carried into effect, reference will now be made, by way of example, to the accompanying drawings, which illustrate aspects of embodiments of the present invention and in which:

FIG. 2A is schematic drawing showing details of the hollow fiber filter bundle 660a shown in apparatus 600a, which is shown collectively in FIGS. 1A-1D;

FIG. 2B is the left side view of the hollow fiber filter bundle 660a shown in FIG. 2A;

FIG. 2C is the right side view of the hollow fiber filter bundle 660a shown in FIG. 2A;

FIG. 2D is a cross-sectional view through the hollow fiber filter bundle 660a shown in FIG. 2A along line D-D;

FIG. 2E is a perspective view of the hollow fiber filter bundle 660a;

FIG. 2F is a detailed view of the detail F shown in FIG. 2D;

FIG. 2G is an alternative perspective view of the hollow fiber filter bundle 660a;

FIG. 3A is a schematic drawing showing a top view of an apparatus 600b suitable for both extraction of plasma from a whole blood sample, and plasma analyte measurement according to a second embodiment of the invention;

FIG. 3B is a first cross-sectional view through the apparatus 600b shown in FIG. 3A along line B-B;

FIG. 3C is a second cross-sectional view through the apparatus 600b shown in FIG. 3A along line C-C;

FIG. 3D is a third cross-sectional view through the apparatus 600b shown in FIG. 3A along line D-D;

FIG. 3E is a fourth cross-sectional view through the apparatus 600b shown in FIG. 3B along line E-E;

FIG. 3F is a detailed view of the detail F shown in FIG. 3C;

FIG. 4A is a schematic drawing showing details of a top view of an apparatus 600c suitable for both extraction of plasma from a whole blood sample, and plasma analyte measurement according to a third embodiment of the invention;

FIG. 4B is a first cross-sectional view through the apparatus 600c shown in FIG. 4A along line B-B;

FIG. 4C is a second cross-sectional view through the apparatus 600c shown in FIG. 4A along line C-C;

FIG. 4D is a third cross-sectional view through the apparatus 600c shown in FIG. 4B along line D-D;

FIG. 5A is schematic drawing showing details of a hollow fiber filter bundle 660b shown in apparatus 600c, which is shown collectively in FIGS. 4A-4D;

FIG. 5B is a perspective view of the hollow fiber filter bundle 660b shown in FIG. 5A;

FIG. 5C is an alternative perspective view of the hollow fiber filter bundle 660b shown in FIG. 5A;

FIG. 5D is a cross-sectional view through the hollow fiber filter bundle 660b shown in FIG. 5A along line D-D;

FIG. 5E is a detailed view of detail E shown in FIG. 5D;

FIG. 6A is a schematic drawing showing details of the top view of an apparatus 600d suitable for both extraction of plasma from a whole blood sample, and plasma analyte measurement according to a fourth embodiment of the invention;

FIG. 6B is a first cross-sectional view through the apparatus 600d shown in FIG. 6A along line B-B;

FIG. 6C is a second cross-sectional view through the apparatus 600d shown in FIG. 6A along line C-C;

FIG. 6D is a third cross-sectional view through the apparatus 600d shown in FIG. 6A along line D-D;

FIG. 6E is a fourth cross-sectional view through the apparatus 600d shown in FIG. 6D along line E-E;

FIG. 7A is a schematic drawing showing details of the top view of an apparatus 600e suitable for both extraction of plasma from a whole blood sample, and plasma analyte measurement according to a fifth embodiment of the invention;

FIG. 7B is a cross-sectional view through the apparatus 600e shown in FIG. 7A along line B-B;

FIG. 7C is a perspective view of the apparatus 600e;

FIG. 8A is a schematic drawing showing details of a top view of a needle 100 that can be used with the apparatus 600d shown collectively in FIGS. 6A-6E;

FIG. 8B is a left side view of the needle 100 shown in FIG. 8A;

FIG. 8C is a right side view of the needle 100 shown in FIG. 8A;

FIG. 8D is a cross-sectional view through the needle 100 shown in FIG. 8A along line D-D;

FIG. 8E is a perspective view of the needle 100;

FIG. 8F is an alternative perspective view of the needle 100;

FIG. 9A is a schematic drawing showing details of a top view of a barrel 200 for a needle 100 shown collectively in FIGS. 8A-8F, for sheathing and unsheathing the needle;

FIG. 9B is a left side view of the barrel 200 shown in FIG. 9A;

FIG. 9C is a first cross-sectional view through the barrel 200 shown in FIG. 9A along line C-C;

FIG. 9D is a right side view of the barrel 200 shown in FIG. 9A;

FIG. 9E is a second cross-sectional view through the barrel 200 shown in FIG. 9A along line E-E;

FIG. 9F is a perspective view of the barrel 200;

FIG. 10A is a schematic drawing showing details of a top view of an assembly 300 of the needle 100 (shown collectively in FIGS. 8A-8F) and the barrel 200 (shown collectively in FIGS. 9A-9F), with the needle retracted into the barrel;

FIG. 10B is a left side view of the assembly 300 shown in FIG. 10A;

FIG. 10C is a right side view of the assembly 300 shown in FIG. 10A;

FIG. 10D is a cross-sectional view through the assembly 300 shown in FIG. 10A along line D-D;

FIG. 10E is a perspective view of the assembly 300;

FIG. 10F is an alternative perspective view of the assembly 300;

FIG. 11A is a schematic drawing showing details of the top view of an apparatus 600f suitable for both extraction of plasma from a whole blood sample, and plasma analyte measurement according to a sixth embodiment of the invention;

FIG. 11B is a first cross-sectional view through the apparatus 600f shown in FIG. 11A along line B-B;

FIG. 11C is a second cross-sectional view through the apparatus 600f shown in FIG. 11B along line C-C;

FIG. 12A is a schematic drawing showing details of a front view of a meter 900 that can be used with some embodiments of the whole blood and plasma apparatus;

FIG. 12B is a first cross-sectional view through the meter 900 shown in FIG. 12A along line B-B;

FIG. 12C is a second cross-sectional view through the meter 900 shown in FIG. 12A along line C-C;

FIG. 12D is a perspective view of the meter 900;

FIG. 13A is a schematic drawing showing details of a front view of a meter slot 800 from a meter 900, which is shown collectively in FIGS. 12A-12D;

FIG. 13B is a cross-sectional view through the meter slot 800 shown in FIG. 13A along line B-B;

FIG. 13C is a perspective view of the meter slot 800;

FIG. 14A is a schematic drawing showing details of the top view of an apparatus 600g suitable for both extraction of plasma from a whole blood sample, and plasma measurement according to a seventh embodiment of the invention;

FIG. 14B is a first cross-sectional view through the apparatus 600g shown in FIG. 14A along line B-B;

FIG. 14C is a second cross-sectional view through the apparatus 600g shown in FIG. 14B along line C-C;

FIG. 15A is a schematic drawing showing details of the top view of a combined apparatus (600h) and cap (960) 600k, suitable for both extraction of plasma from a whole blood sample, and plasma measurement according to a eight embodiment of the invention;

FIG. 15B is a first cross-sectional view through the combined apparatus and cap 600k shown in FIG. 15A along line B-B;

FIG. 15C is a second cross-sectional view through the combined apparatus and cap 600k shown in FIG. 15B along line C-C;

FIG. 15D is a perspective view of the combined apparatus and cap 600k; and

FIG. 15E is an alternative perspective view of the combined apparatus and cap 600k.

DETAILED DESCRIPTION OF PREFERRED ASPECTS OF THE INVENTION

Figures 1A, 1B, 1C, 1D:
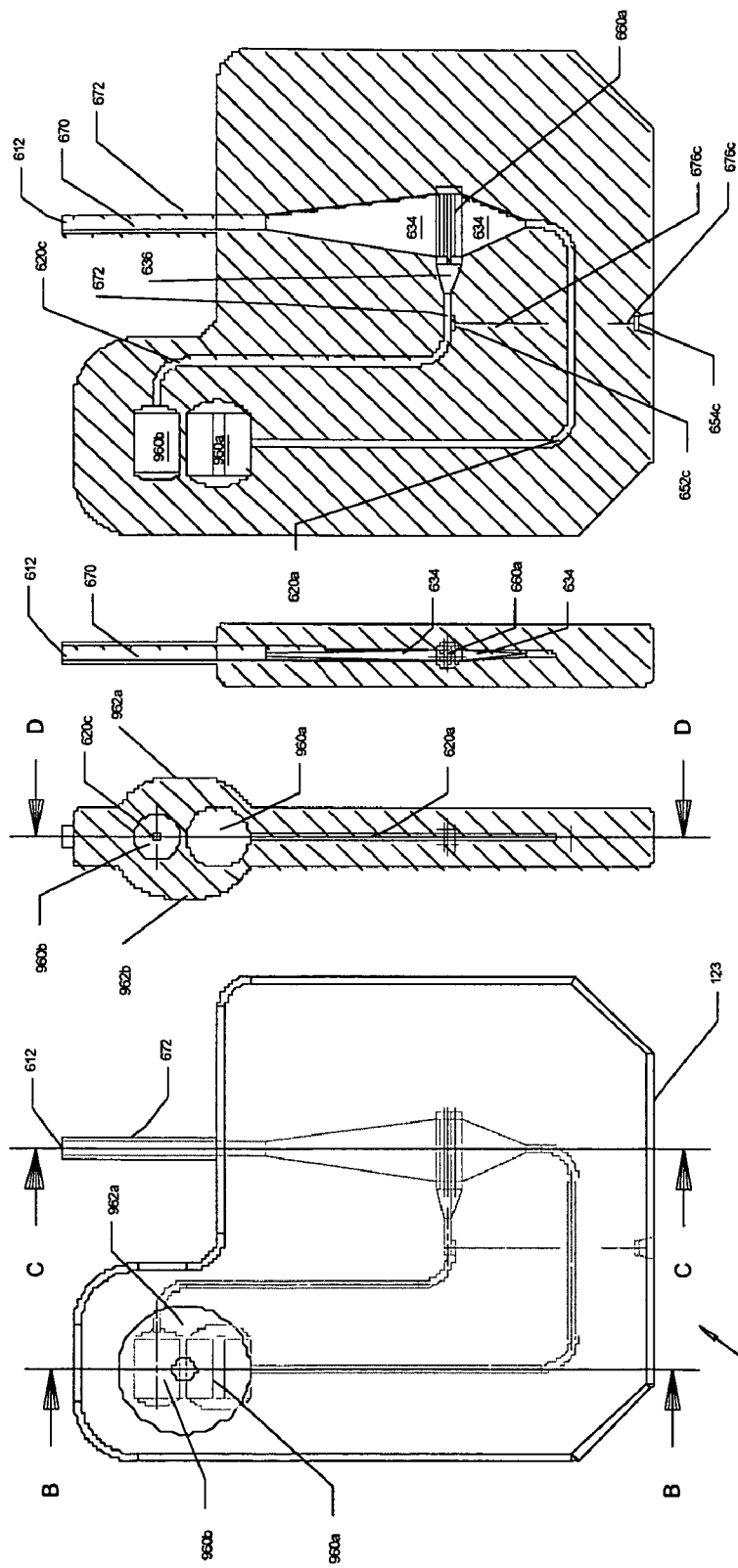
FIG. 1A is a schematic drawing showing details of a top view of an apparatus 600a suitable for both extraction of plasma from a whole blood sample, and plasma analyte measurement according to a first embodiment of the invention.
FIG. 1B is a first cross-sectional view through the apparatus 600a shown in FIG. 1A along line B-B.
FIG. 1C is a second cross-sectional view through the apparatus 600a shown in FIG. 1A along line C-C.
FIG. 1D is a third cross-sectional view through the apparatus 600a shown in FIG. 1B along line D-D.

Some embodiments of the invention provide one disposable apparatus that is suitable for both the extraction of plasma from a whole blood sample, and facilitating measurement of the plasma in the apparatus, using a suitable meter, for example without limitation, the meter 900 shown collectively in FIGS. 12A-12D. In addition, some embodiments of the apparatus are used for collection of a blood sample directly from a body part.

The disposable apparatus comprises at least one whole blood flow path and one plasma flow path, for example apparatus 600a shown collectively in FIGS. 1A-1D. Those skilled in the art will appreciate that the apparatus could comprise more than two flow paths, for example, apparatus 600f shown collectively in FIGS. 11A-11C comprises two whole blood flow paths and one plasma flow path. A flow path is defined by a start end and a terminating end, and includes at least one chamber in fluid connectivity with the start end and a terminating end. Any other chambers in the flow path must be in series and in fluid connectivity with each other. Flow paths are identified in the examples shown.

Since one function of the apparatus is to extract or filter plasma out of whole blood, the plasma flow path also represents a plasma compartment, and one or more blood flow path represents a blood compartment; the plasma compartment and the blood compartment are separated by a membrane. This compartmentalization of blood and plasma is better understood when the membrane 694 is flat, as illustrated collectively in FIGS. 3A-3F. It should be understood that although the hematocrit of the whole blood is altered after plasma filters through the membrane, the blood with the altered hematocrit is still referred to as whole blood (or blood). A second function of the apparatus is to generate and provide signals to the meter processor for measurement of at least one analyte in the extracted plasma. In the examples described, the signal providing means include at least an optical chamber having at least one optical window for performing spectroscopic measurement (or spectroscopy), or a biosensor chamber comprising at least one biosensor in contact with the plasma.

Depending on the design of the apparatus, as will be seen from the examples described later in details, the blood sample can enter the apparatus for measurement by any of the following means, or combination thereof: a) negative pressure generating means in a flow path, for example, negative pressure can be generated by squeezing and releasing a compressible suction chamber (also referred to as a suction chamber) located at the end of the flow path; b) capillary action; c) positive pressure from the plunger in a syringe containing the sample; and d) positive pressure from blood within a blood vessel, for example, capillaries, veins, and arteries. Positive pressure from a blood vessel is particularly useful when the inlet opening of the apparatus is a sharp open end 147 of a needle, illustrated collectively in FIGS. 7A-7C, as a non-limiting example. The positive pressure from a syringe is usually applied at the inlet opening of the apparatus, for example, inlet opening 612 of apparatus 600d, illustrated collectively in FIGS. 6A-6E.

An essential feature of the apparatus is a flow-through filtration chamber comprising a filtration membrane, sometimes simply referred to as a membrane. The membrane has optional shapes and sizes, and includes a wall with a wall thickness, and pores through the wall of the membrane. Moreover, the membrane can be assembled in different ways, as shown in the examples. Plasma filtration is enhanced by the following: increased blood flow; increased size and number of pores in the membrane; decreased membrane wall thickness; and increased surface area of the membrane. Those skilled in the art will appreciate that these features should be optimized for efficient plasma filtration, for example, increased blood flow decreases the apparent viscosity of the blood; however, if the flow is too forceful, hemolysis could occur. Also, if the pores are too large, red blood cells could filter through with the plasma and furthermore, the red blood cells could plug up the pores and hinder plasma filtration.

The measurement techniques shown as non-limiting examples include spectroscopic measurement and biosensor measurement. The terms testing a sample, and analyzing a sample, are sometimes used instead of the term measuring a sample, and those skilled in the art will appreciate that these terms mean, providing information about a sample, for example, the bilirubin (an analyte) concentration in the sample, or the ratio of two different analytes. Optionally, some embodiments provide measurements of both plasma and the whole blood used to provide the plasma.

Some embodiments of the meter may include the following:

a) a meter housing;

b) a power supply, which is preferably in the form of rechargeable batteries;

c) a source of electromagnetic radiation (EMR);
d) a slot in the meter housing for receiving the apparatus, the slot having an electrical input contact for mating with the electrical output contact of the apparatus when the apparatus is inserted into the slot. When the electrical input contact mates with the electrical output contact of the apparatus, the optical chamber becomes positioned to receive the EMR from the source. Also, when the electrical input contact mates with the electrical output contact of the apparatus, and with the sample is in contact with the biosensor, sample biosensor data is generated;
e) a photodetector for measuring EMR transmitted through or reflected from the fluid sample within the optical chamber and for providing an EMR-based signal derived from the EMR transmitted through or reflected from the fluid sample; and
f) a processor in communication with the photodetector for receiving the EMR-based signal, and the input contact for receiving the sample biosensor data. The EMR-based signal is used to prepare a spectroscopic test result, and the sample biosensor data is used to prepare a biosensor test result. A test result is also referred to as an analyte measurement.

Some embodiments of the meter comprise one photodetector or photodiode, or more than one photodetector assembled as an array of detectors in a spectrometer. A spectrometer using an array of detectors also comprises a grating for dispersing EMR emerging from the fluid sample, into wavelength components. The meter optionally comprises a focusing lens between the apparatus and the spectrometer, show as 870 in FIGS. 12A & 12C and FIGS. 13A & 13C. Some embodiments of the meter only perform spectroscopic measurements, and the signal providing means in the apparatus comprises an optical chamber within the housing of the apparatus, for receiving the extracted plasma, the optical chamber having at least one optical window for spectroscopic measurement. Alternatively, some embodiments of the meter only perform biosensor measurements, and the signal providing means in the apparatus comprises biosensor chamber within the housing of the apparatus, for receiving the extracted plasma, the biosensor chamber having at least one biosensor for biosensor measurement.

The biosensor chamber is located along a flow path, and the biosensor chamber may have one or more than one biosensor for analyzing the plasma sample. Optionally, the apparatus contains more than one biosensor chamber as illustrated in FIG. 6E, identified as 672 (a plasma biosensor chamber) and 674 (a whole blood biosensor chamber). A flow path that includes a biosensor chamber is specifically designed with at least one active surface of the biosensor exposed to the sample. Those skilled in the art will appreciate that biosensors may include various transducer arrangements that convert at least one property of the sample into an electrical signal, wherein the transducer comprises at least one active surface for contacting the sample. The at least one active surface is one of a chemical sensitive surface, or an ionic sensitive surface, and wherein the at least one biosensor comprises at least one of a transistor, an ion-selective membrane, a membrane-bound enzyme, a membrane-bound antigen, a membrane-bound antibody, or a membrane-bound strand of nucleic acid. The apparatus also comprises at least one electrical output contact, for example 654c illustrated in FIG. 1D, which is electrically connected to the biosensor 652c by an electrical conductor 676C. The apparatus slot of the meter, for example 800 illustrated collectively in FIGS. 12A-13C comprises two electrical input contacts 854a and 854b. When the electrical output contacts from a suitable apparatus mate with a corresponding electrical input contact after the apparatus is properly inserted into the slot, the optical chamber is positioned to receive EMR from its source. Although the example shows the apparatus electrical output contact in a female configuration, and also shows the meter slot electrical input contact in a male configuration, those skilled in the art will appreciate that the electrical output contacts can mate with the electrical input contacts in other ways.

In some embodiment of apparatus, the biosensors require calibration prior to sample measurement, and some biosensors are pre-calibrated. Pre-calibration is usually performed for a lot or batch of apparatus, and a barcode on the apparatus could contain calibration information, which is read by a barcode reader that is linked to the processor of the meter. In the embodiments of disposable apparatus that require calibration prior to sample measurement, calibration of biosensors is performed by flooding the biosensor chamber with an appropriate calibration fluid stored in a sealed calibration reservoir or pouch in a cavity of the apparatus (not shown). In an embodiment of the meter where calibration of the biosensor is required for the individual apparatus, prior to sample measurement, the meter also comprises a means for rupturing the calibration pouch and delivering the calibration fluid to the biosensor(s) in the biosensor chamber. Those skilled in the art will appreciate that the electrical signals generated from the biosensor after it comes in contact with a calibration fluid of know composition, and the known concentration of the analyte in the calibration fluid, can be used to generate a calibration algorithm for the analyte, and therefore for the sake of brevity, the mathematics involved in biosensor calibration will not be discussed here. The biosensor calibration requires mating of the electrical output contact of the apparatus and the electrical input contact of the meter slot.

Moreover, where calibration of the biosensor is required, capillary breaks are provided along the flow path at strategic locations, for retaining the calibration fluid in the biosensor chamber (not shown). Sometimes a capillary break, located along the flow path between the inlet opening and the biosensor chamber (not shown), is used to retain the fluid sample away from the biosensor, prior to sample measurement. A capillary break is defined as an expansion in the flow path, which makes the flow path too large at the point of expansion to maintain fluid flow by capillary action. In some embodiments, where flow does not depend on capillary action, references are still made to capillary breaks. In such cases, the structure referred to as a capillary break, is simply an expansion in the flow path that functions as a buffer chamber for collecting excess fluid. After biosensor calibration, the fluid sample is used to flush out the calibration fluid from the biosensor chamber, and bring the fluid sample in contact with the biosensor. Those skilled in the art will appreciate the methods used to flush out the calibration fluid with sample, and for the sake of brevity, the methods will not be discussed here.

Some embodiments of apparatus are shown with vents for relieving pressure inside the flow paths, or facilitating airflow out of the flow paths. Other embodiments of the apparatus are shown, where there are no vents for facilitating airflow out of the flow path. Instead of the vent, the housing of the apparatus includes a compressible suction chamber located at the end of the flow path, replacing the vent(s), and means for generating negative pressure within the suction chamber. In some embodiments, two separate suction chambers (for example 960a and 960b shown in FIG. 4D) are located close to each other, without being fluidly connected, so that one set of flexible members (for example 962a and 962b shown in FIG.

4B) can be used to generate negative pressure simultaneously in the two separate suction chambers. In some embodiments, two or more suction chambers are fluidly connected or merged into one suction chamber. It should be understood that having two suction chambers fluidly connected, is equivalent to merging the two suction chambers into one suction chamber. Those skilled in the art will appreciate that other embodiments of apparatus can operate with a combination of at least one vent and at least one suction chamber, and a single flexible member, for example, 962a or 962b, can be used to compress the vacuum chamber.

In some embodiments, the interior walls of the apparatus are treated with a hydrophillic coating to promote even spreading of the blood within the optical chamber, and to promote movement of blood along the flow path. A flow path may also contain one or more reagents, anywhere along the flow path, for example without limitation, an anticoagulant, a hemolyzing reagent, or a reagent that reacts with an analyte to enhance the absorbance of EMR. In some use of the apparatus, anticoagulated blood is collected in a microtube, for example, blood collected from the heel of a neonate after a pin or lancet prick, for diagnosing and treating neonatal jaundice. Ordinarily the blood is sent to the central lab for centrifugation, and bilirubin is measured in the plasma using a lab blood analyzer. In this example, there is no need for an anticoagulant anywhere inside the apparatus, because the blood is already collected in a microtube containing an anticoagulant.

In using the anticoagulated blood from the neonate, a preferred embodiment of the apparatus is one like apparatus 600h, illustrated collectively in FIGS. 15A-15E. Before drawing the blood into the apparatus 600h, the flexible members 962a and 962b are squeezed between the fingers of the user in order to dispel air from the suction chambers 960a and 960b. Subsequently, the inlet opening 612 is inserted inside the blood sample in the microtube. Those skilled in the art will appreciate that the length of the piece of capillary tubing 672 must be optimized so that the inlet opening can at least reach close to the bottom of the microtube, and to provide a blood barrier between the filtration chamber 634 and the atmosphere. The blood barrier will prevent air from being sucked into the plasma measurement chamber, for example, the optical chamber 616b (FIG. 15C).

Once the inlet opening 612 is submerged in the blood contained in the microtube, pressure on the suction chambers 960a and 960b is released slowly, allowing blood to be drawn into the blood flow path, and plasma to be filtered into the plasma flow path. Those skilled in the art will appreciate that the draw from the suction chambers 960a and 960b, and the rebound of the flexible members 962a and 962b could be optimized, so that the pressure on the flexible members 962a and 962b does not have to be released slowly. In a particular embodiment, the draw from suction chamber 960a is greater than the draw from the suction chamber 960b.

Preferably, the plasma flow path, and in particular the inside walls of the optical chamber 616b, is coated with a hydrophilic material, in order to promote even spreading of the plasma in the optical chamber 616b. Those skilled in the art will appreciate that calibration algorithm for the spectroscopic measurement of bilirubin, as a non-limiting example, can be developed using calibration samples containing air bubbles in the optical chamber 616b, enabling the meter to measure bilirubin in samples with inclusion of air bubbles in the optical chamber, with minimal errors.

When an apparatus comprising both facilities for spectroscopic measurement and facitilities for biosensor measurement is inserted properly in the slot of the meter, the electrical output contact of the apparatus mates with the electrical input contact of the meter slot, bringing the optical chamber of the apparatus in position to receive EMR from the EMR source. Those skilled in the art will appreciate that the EMR could also be channeled to the optical chamber by optical fibers. The EMR transmitted through the fluid sample in the apparatus, or reflected from the fluid sample, impinges upon a photodetector within the meter. Calibration algorithms for spectroscopic measurements are preferably installed within the processor of the meter, for transforming the spectroscopic signals into analyte measurements. Calibration algorithms for biosensor measurements are preferably installed within the processor of the meter, for transforming the biosensor signals into analyte measurements, but some biosensors require calibration prior to sample measurement.

Those skilled in the art will appreciate the various ways a spectroscopic measurement instrument can be constructed, and various elements that make up such instruments. Accordingly, for the sake of brevity, description of basic spectroscopy and a list and function of the elements that make up a spectroscopic device will not be discussed here. However, it should be noted that a joint-diagnostic spectroscopic and biosensor meter, requires at least one source of EMR, and the preferred source of EMR is a tungsten lamp, but without limitation, the source of EMR may include one or more than one Light Emitting Diode (LED), or one or more than one laser, or combination thereof. Those skilled in the art will appreciate that when the source of EMR is a single source, the single source could be split by a multi-channel optical fiber for providing more than one light path.

With respect to the detection system, the preferred detector is an array of photodiodes, but those skilled in the art will appreciate that a single photodiode or one or more than one charged coupled detector (CCD) can be used.

With respect to spectroscopic measurements, the examples shown describe a meter that operates in transmission mode. Those skilled in the art will appreciate that the meter can also operate in reflectance mode by placing a reflecting member in the apparatus slot, on one side of the optical chamber 616b (FIG. 15A and FIG. 15C), such that the EMR transmitted through the sample would be reflected off the reflecting member, and the reflected EMR would enter the sample for the second time. In a meter operating in the reflectance mode, both the EMR source and the photodetector would be on the same side of the optical chamber 616b. Moreover, those skilled in the art will also appreciate that instead of installing a reflecting member around the slot in the housing of the meter, one side of the wall-portions 626a or 626b of the optical chamber 616b, for example as shown in FIGS. 15A-15E, could be coated with a reflecting material. Preferably the depth of the optical chamber, i.e., the internal distance between the optical windows, is about 0.1 mm for a blood sample, but the depth of the optical chamber is preferably larger for plasma, due to the absence of red blood cells. An average depth of an optical chamber is in an approximate range of about 0.02 mm to about 5 mm.

In some embodiments, the meter further comprises a display screen for viewing the results and aiding the operator in use of the meter, as well as buttons for manipulating the display function. Those skilled in the art will appreciate that the meter could be connected to a host computer. Therefore, some embodiments of the system also comprise at least one communication port for interfacing with other instruments. Other non-limiting examples of other instruments are a printer, and diagnostic testing instruments like a pulse oximeter or some other non-invasive testing instrument. The optional communication port is also used to upgrade information in the meter's processor, as well as to download information from the meter's processor. Another optional port in the housing of some embodiments of the joint-diagnostic spectroscopic and biosensor meter is provided for charging the power supply within the meter. Those skilled in the art will appreciate that a single port can be used for both data transfer and a power supply, for example without any limitation, a USB (Universal Serial Bus) port.

In a specific embodiment of a apparatus illustrated collectively in FIGS. 1A-1D, the apparatus contains a flow-through filtration chamber, which comprises a hollow fiber filter bundle 660a. Details of the hollow fiber filter bundle 660a are illustrated collectively in FIGS. 2A-2G. The hollow fiber filters may run in parallel with the flow path within the filtration chamber, as illustrated as 660b in FIGS. 4C & D, but in a preferred embodiment, illustrated collectively in FIGS. 15A-15E for example, the hollow fiber filters in the bundle 660a run approximately orthogonal to the whole blood flow path.

In some embodiments, the inlet chamber 670 of the apparatus illustrated collectively in FIGS. 6A-6E is dimensioned to accommodate a male end of a traditional syringe. In other embodiments, the inlet of the apparatus is also dimensioned to resemble the end of a capillary tubing, for example 672 illustrated collectively in FIGS. 1A-1D, to receive the blood sample from a pin prick drop of blood. As an alternative, the inlet of the apparatus is the sharp end 147 of a needle, as illustrated collectively in FIGS. 7A-7C. The needle is allowed to enter the lumen of a blood vessel for receiving the blood directly into the apparatus, eliminating the need of a syringe. The sharp end 147 of the needle 100 is preferably encased in a moveable barrel 200, illustrated collectively in FIGS. 9A-9F, for sheathing and unsheathing the sharp end of the needle, to protect the user from accidental injury. An example of a needle, barrel, and the assembly of the two, which should not be considered limiting in any way, are illustrated collectively in FIGS. 8A-8F, FIGS. 9A-9F and FIGS. 10A-10F respectively. Other embodiments of similar needles are disclosed in Canadian Patent Application No. 2,517,299 (Samsoondar, the entire contents of which are incorporated herein by reference). The outlet 171 of the needle assembly 300, illustrated collectively in FIGS. 10A-10F, mates with the inlet chamber 670 of the apparatus illustrated collectively in FIGS. 6A-6E, eliminating the need of a syringe. The apparatus could be inserted into the meter slot, with the needle still attached. As another alternative, as illustrated collectively in FIGS. 14A-14E, the inlet chamber 670 is flared so that the inlet opening 612 can be placed over a pin prick, either before but preferably after the drop of blood develops. The blood is then allowed to freely flow into the apparatus. The flow may be assisted by some squeezing of the body part around the pin prick. It is well known that excessive squeezing, commonly referred to as milking, should be avoided if contamination of the blood with interstitial fluid compromises the accuracy of the analyte measurement.

In an embodiment illustrated in FIG. 11A, comprising several measurement chambers, the distance from the blood optical chamber to its adjacent edge (A) of the apparatus, is approximately equal to the distance from the plasma optical chamber to its adjacent edge (B) of the apparatus. An embodiment of a meter designed to operate with such an apparatus, could comprise one source of EMR and one light path. The EMR in the single light path travels through the first optical chamber when the apparatus is inserted properly in a first orientation. When the apparatus is inserted properly in a second orientation, the second orientation being 180 degrees to the first orientation, the single light path travels through the second optical chamber. Therefore, the plasma and the whole blood can be measured sequentially using the same light path. Because of the absorbance signals for whole blood and plasma are significantly different, the software in the meter could discriminate whole blood from plasma. Those skilled in the art will appreciate that there are other methods of analyzing the plasma and whole blood using a single light path, for example, a prompt in the display screen could provide appropriate instructions for insertion of the apparatus.

Referring collectively to FIGS. 1A-1D, shown are schematic drawings illustrating details of an apparatus 600a that is suitable for both extraction of plasma from a whole blood sample, and plasma measurement according to a first embodiment of the invention.

Referring to FIG. 1A is a schematic drawing showing a top view of the apparatus 600a; FIG. 1B is a first cross-sectional view through the apparatus 600a shown in FIG. 1A along line B-B; FIG. 1C is a second cross-sectional view through the apparatus 600a shown in FIG. 1A along line C-C; and FIG. 1D is a third cross-sectional view through the apparatus 600a shown in FIG. 1B along line D-D. The apparatus 600a includes a housing 123, defining: a whole blood flow path beginning at the inlet opening 612 (the start end), and terminating at the suction chamber 960a (the terminating end); and a plasma flow path beginning at the plasma collection chamber 636 (the start end) and terminating at the suction chamber 960b (the terminating end). As shown in the whole blood flow path in series, are the inlet opening 612, the inlet chamber 670 for receiving blood through the inlet opening 612, the flow-through filtration chamber 634, the filtration chamber outflow 620a, and the suction chamber 960a, in fluid connectivity. The filtration chamber 634 comprises the hollow fiber bundle 660a, which is shown in details in FIGS. 2A-2G. As shown in the plasma flow path in series, are the plasma collection chamber 636, the plasma biosensor chamber 672 (the plasma measurement chamber), the plasma biosensor chamber outflow 620c, and the suction chamber 960b, in fluid connectivity. Regarding the whole blood flow path, those skilled in the art will appreciate that the inlet chamber 670, the filtration chamber 634, and the outflow 620a may be considered collectively as the filtration chamber. Regarding the plasma flow path, those skilled in the art will appreciate that the plasma collection chamber 636, the plasma biosensor chamber 672, and the plasma outflow 620c may be considered collectively as the plasma collection chamber. Moreover, those skilled in the art will also appreciate that although some parts shown are not essential, or two or more parts overlap, the various parts are sometimes included for clarity. In the embodiment of the apparatus 600a, the measurement technique uses a single biosensor, but other embodiments include more than one biosensor, and some embodiments include an optical chamber for spectroscopic measurement, instead of a biosensor chamber. As an example, an optical chamber 616b is shown in the embodiment 600b, illustrated collectively in FIGS. 3A-3F.

With further reference to FIGS. 1A-1D, shown is the filtration chamber outflow 620a, terminating at the suction chamber 960a. The suction chamber 960a is a cavity in the housing 123 with flexible members 962a and 962b. By manually squeezing and releasing the flexible members 962a and 962b, negative pressure is generated in the suction chambers 960a and 960b. The only opening in apparatus 600a is the inlet opening 612, and those skilled in the art will appreciate that the inlet opening 612 can be capped to avoid contaminating the apparatus with blood. As a non limiting example, a cap 960 is illustrated collectively in FIGS. 15A-15E. Those skilled in the art will appreciate that one flexible member (962a or 962b) could perform the same function. In this embodiment, by squeezing the flexible members 962a and 962b, negative pressure is also generated in both suction chambers 960a and 960b, for ease of use. The volume of the suction chambers 960a and 960b, and the maximum depression of the flexible members 962a and 962b, determines the maximum volume of fluids that could be drawn into the flow paths. Also, the rigidity of the flexible members 962a and 962b, which contributes to the rate at which the members 962a and 962b are restored to their original shape after squeezing and releasing (the rebound of the flexible members 962a and 962b), determines the velocity of the fluids in the flow paths. In some embodiments, for example apparatus 600f illustrated collectively in FIGS. 11A-11C, the three flow paths converge into a single suction chamber 960d. Those skilled in the art will appreciate that in another embodiment, suction chambers 960a and 960b could be merged into a single suction chamber.

To test a patient's blood, the flexible members 962a and 962b must first be squeezed, preferably between two fingers, to dispel air from the suction chambers 960a and 960b. With air inside the suction chambers 960a and 960b dispelled, the inlet opening 612 of the apparatus 600a is then inserted into a blood sample, which could be a drop of blood on the patient's skin, generated from a pin prick, or anticoagulated blood in a microtube (a small tube, usually used for neonatal blood collection). To draw the blood into the apparatus 600a, the flexible members 962a and 962b must be released, creating negative pressure within the suction chambers 960a and 960b. Preferably, the flexible members 962a and 962b are released slowly, to maintain the inlet chamber 670 filled with blood. The negative pressure within the suction chamber 960a causes blood to flow in the blood flow path towards the suction chamber 960a; the blood flow decreases the apparent viscosity of the blood and reduces compaction of the red blood cells in the filter. The extraction of plasma from the blood is enhanced by: capillary action within the various chambers defined in the housing 123, the negative pressure created in the suction chamber 960b, the negative pressure created in the suction chamber 960a, the surface area of the hollow fiber filters in bundle 660a, the pore size in the membrane 694, and the wall thickness of the membrane 694 (FIGS. 2F & 3F). The surface area of the hollow fiber filters in bundle 660a is increased by increasing the number of hollow fiber filters.

Referring collectively to FIGS. 2A-2G, shown are schematic drawings illustrating details of the hollow fiber filter bundle 660a shown inside the plasma filtration chamber 634 illustrated collectively in FIGS. 1A-1D. The hollow fiber filter bundle 660a in this embodiment comprises seven hollow fiber filters, held together by two flanges 682 and 684.

Referring to FIG. 2A, shown is a top view of the hollow fiber filter bundle 660a, illustrating the perforated flange 684, and the closed flanged 682, and identifying a single hollow fiber 696.

FIG. 2B, shown is a left side view of the hollow fiber filter bundle 660a, illustrating the perforated flange 684, and identifying the lumen 692 of a single hollow fiber filter.

Referring to FIG. 2C, shown is a right side view of the hollow fiber filter bundle 660a, illustrating the closed flange 682. The periphery of the flanges 682 and 684 are sealed in the body 123 of the apparatus, to prevent blood from entering the plasma compartment. Therefore, the only contact between blood and the plasma extracted from the blood is through the pores in the wall 694 of the membrane. In this embodiment of the apparatus, the flanges are a schematic representation of the seal between the blood compartment and the plasma compartment. From a manufacturing perspective, it is preferred that the hollow fiber filters be assembled in bundles as shown, and sandwiched in position between the top and bottom halves of the apparatus.

Referring to FIG. 2D, shown is a cross-sectional view through the bundle 660a shown in FIG. 2A along line D-D, showing the closed flange 682, the cross-section of the hollow fiber filters, and detail F.

Referring to FIG. 2E, shown is a perspective view of the hollow fiber filter bundle 660a, showing a clear view of the perforated flange 684.

Referring to FIG. 2F, shown is a detailed view of the cross-section of a single hollow fiber, according to detail F identified in FIG. 2D, showing the lumen 692 of the hollow fiber, and the wall 694 of the fiber.

Referring to FIG. 2G, shown is an alternative perspective view of the hollow fiber filter bundle 660a, showing a clear view of the closed flange 682. As an example, seven hollow fiber filters are shown tightly inserted inside perforations in the flange 684, and sealed at the juncture of the hollow fibers and the flange 682. The wall 694 of the fiber is porous, and in some embodiments, the pores have an approximate distribution of pore diameters ranging from about 0.1 micrometer to about 30 micrometers, and in some embodiments the thickness of the wall 694 ranges from about 0.1 mm to about 0.5 mm. In some embodiments, the internal diameter of the hollow fiber filters ranges approximately from about 0.1 mm to about 1 mm. Those skilled in the art will appreciate that various combination of pore sizes, wall thicknesses, and internal diameters of the hollow fiber filters could be used, depending on the method used to draw the blood and plasma along their flow paths.

Those skilled in the art will appreciate the membrane 694 is a partition between the blood compartment, and the plasma compartment. In this embodiment, the blood compartment is represented by the filtration chamber 634, and the plasma compartment is represented by the plasma collection chamber 636. In this embodiment of the invention, the plasma compartment includes the lumen 692 of the hollow fiber filters, and the blood compartment includes the exterior of the hollow fiber filters. A reversed design is illustrated collectively in FIGS. 4A-4D, where the blood compartment includes the lumen of the hollow fiber filters, both flanges identified as 684a and 684b (illustrated collectively in FIGS. 5A-5E) are perforated, and the plasma compartment includes the exterior of the hollow fiber filters. The blood and plasma compartment are more clearly seen in a second embodiment of the apparatus (600b), illustrated collectively in FIGS. 3A-3F. In apparatus 600b, the membrane 694 is not arranged as hollow fiber filters, but instead is a flat member erected as a partition between the blood compartment (illustrated as the chamber 634) and the plasma compartment (illustrated as the chamber 636a). These embodiments will be described in more details later.

In a preferred embodiment, at least the first section of the whole blood flow path is coated with an appropriate anticoagulant, to minimize clotting and promote fluidity of the blood. Fluidity of the blood provides more efficient plasma extraction. However, when the blood sample is anticoagulated blood (i.e., blood mixed with an anticoagulant, for example, heparin) in a tube, an anticoagulant within the flow paths of the apparatus is not essential.

Referring collectively to FIGS. 3A-3F, shown are schematic drawings illustrating details of an apparatus 600b that is suitable for both extraction of plasma from a whole blood sample, and plasma measurement according to a second embodiment of the invention.

Referring to FIG. 3A, shown is a top view of the apparatus 600b; FIG. 3B is a first cross-sectional view through the whole blood and plasma apparatus 600b shown in FIG. 3A along line B-B; FIG. 3C is a second cross-sectional view through the whole blood and plasma apparatus 600b shown in FIG. 3A along line C-C; FIG. 3D is a third cross-sectional view through the whole blood and plasma apparatus 600b shown in FIG. 3A along line D-D; FIG. 3E is a fourth cross-sectional view through the whole blood and plasma apparatus 600b shown in FIG. 3B along line E-E; and FIG. 3F is a detailed view of the detail F shown in FIG. 3C. The apparatus 600b illustrated collectively in FIGS. 3A-3E is similar to the apparatus illustrated collectively in FIGS. 1A-1D, and accordingly, elements common to them share common reference numerals. The first difference is that apparatus 600b has a combination of a vent 137a at the terminating end of the whole blood flow path, and a suction chamber 960c at the terminating end of the plasma flow path. The second difference is that the flow-through filtration chamber comprises a flat membrane 694 instead of the hollow fiber filter bundle 660a shown in FIGS. 1C & 1D. Since the filtration chamber 634 is a section of the whole blood flow path in contact with the membrane 694, the filtration chamber 634 also represents the blood compartment. The plasma collection chamber is represented collectively by chambers 636a and 636b; the chamber identified as 636a represents the section of the plasma compartment that is in contact with the membrane 694. Those skilled in the art will appreciate that chambers 636a and 636b could be considered as a single chamber. The third difference is that in this embodiment, the measurement facility includes an optical chamber 616b for spectroscopic measurement, with optical wall-portions 626a and 626b.

In the embodiment illustrated collectively in FIGS. 3A-3F, capillary action is required for the flow of blood along the whole blood flow path, and negative pressure contributes to plasma extraction and plasma flow. It should be understood that the examples shown do not represent all the possible combinations of vents and suction chambers, and therefore, the examples should not limit the scope of the present invention.

Referring collectively to FIGS. 4A-4D, shown are schematic drawings illustrating details of an apparatus 600c that is suitable for both extraction of plasma from a whole blood sample, and plasma measurement according to a third embodiment of the invention.

Referring to FIG. 4A, shown is a top view of the apparatus 600c; FIG. 4B is a first cross-sectional view through the apparatus 600c shown in FIG. 4A along line B-B; FIG. 4C is a second cross-sectional view through the apparatus 600c shown in FIG. 4A along line C-C; and FIG. 4D is a third cross-sectional view through the apparatus 600c shown in FIG. 4B along line D-D. The apparatus 600c illustrated collectively in FIGS. 4A-4D is similar to apparatus 600a illustrated collectively in FIGS. 1A-1D, and accordingly, elements common to them share common reference numerals. The major difference is that the fiber bundle 660b, illustrated collectively in FIGS. 5A-5E in details, comprise perforated flanges on both ends (684a and 684b), and the whole blood flows through the hollow fiber filters instead of around the hollow fiber filters. A second difference is the plasma measurement facility comprises an optical chamber 616b shown in FIG. 4D. Those skilled in the art will appreciate that the lumen 692 (FIG. 5D) of the hollow fiber filters must be larger than the lumen in the embodiment illustrated in FIGS. 2A-2G, to avoid compaction of red blood cells in the lumen of the hollow fiber filters. In a preferred embodiment, blood flows approximately orthogonal to the hollow fiber filters, and the plasma is extracted into the lumen of the fibers.

Referring collectively to FIGS. 5A-5E, shown are schematic drawings illustrating details of an embodiment of a hollow fiber filter bundle 660b shown in apparatus 600c, which is illustrated collectively in FIGS. 4A-4D.

Referring to FIG. 5A, shown is a top view of the hollow fiber filter bundle 660b; FIG. 5B is a perspective view of the hollow fiber filter bundle 660b, showing a first perforated flange 684a in clear view; FIG. 5C is an alternative perspective view of the hollow fiber filter bundle 660b, showing a second perforated flange 684b in clear view; FIG. 5D is a cross-sectional view through the hollow fiber filter bundle 660b shown in FIG. 5A along line D-D; and FIG. 5E is a detailed view of the detail E shown in FIG. 5D. The hollow fiber filter bundle 660b illustrated collectively in FIGS. 5A-5E is similar to the apparatus illustrated collectively in FIGS. 2A-2G, and accordingly, elements common to them share common reference numerals. The major differences are that both flanges 684a and 684b are perforated, and hollow fiber filter bundle 660b comprises four hollow fiber filters instead of seven. Because blood flows inside the hollow fibers in embodiment 660b of a hollow fiber filter bundle, the internal diameter of the fibers must be substantially larger than the internal diameters of the fibers in embodiment 660a, illustrated collectively in FIGS. 2A-2G Referring collectively to FIGS. 6A-6E, shown are schematic drawings illustrating details of an apparatus 600d that is, suitable for both extraction of plasma from a whole blood sample, and whole blood and plasma measurement according to a fourth embodiment of the invention. Referring to FIG. 6A is a top view of the housing 123 of the apparatus 600d showing the sample inlet opening 612, the inlet chamber 670, a whole blood optical chamber wall-portion 624a, and a plasma optical chamber wall-portion 626a. The apparatus 600d comprises three flow paths shown more clearly in FIG. 6E.

Referring to FIG. 6B, shown is a first cross-sectional view through apparatus 600d illustrated in FIG. 6A along line B-B, showing parts identified later in FIG. 6E.

Referring to FIG. 6C, shown is a second cross-sectional view through apparatus 600d illustrated in FIG. 6A along line C-C, showing parts identified later in FIG. 6E. In addition, shown are the conduits 135a, 135b and 135c which connect the capillary breaks 622a, 622b and 622c, with the respective vents 137a, 137b and 137c.

Referring to FIG. 6D, shown is a third cross-sectional view through apparatus 600d illustrated in FIG. 6A along line D-D, showing parts identified later in FIG. 6E. In addition, shown are the blood optical wall portions 624a and 624b. For convenience and as deemed appropriate, same reference numerals are used as those used for the apparatus 600d illustrated previously, and the reference numerals will also be used for other embodiments as deemed appropriate.

Referring to FIG. 6E, shown is a fourth cross-sectional view through apparatus 600d illustrated in FIG. 6D along line E-E. The apparatus 600d can be filled with blood from a traditional syringe, after the male end of the syringe is inserted through the inlet opening 612, into the inlet chamber 670. Alternatively, the male end 171 of the needle 100 illustrated collectively in FIGS. 8A-8F is first fitted into the apparatus inlet chamber 670. Then the sharp open end 147 of the needle is inserted into a blood vessel, allowing the blood to flow into the apparatus 600d. The needle 100 assembled with a safety barrel 200 (shown collectively in FIGS. 9A-9F) is also shown collectively in FIGS. 10A-10F as 300. Whether a traditional syringe or the needle 100 illustrated collectively in FIGS. 8A-8F and FIGS. 10A-10F is used, the blood arrives first at the manifold 640; from the manifold 640, the blood is distributed into two whole blood flow paths, which begin at the manifold 640: the first flow path includes in series, the whole blood biosensor inlet transition chamber 642, the whole blood biosensor chamber 674, the whole blood biosensor outflow chamber 620*b*, the whole blood biosensor capillary break 622*b*, and terminating at the whole blood biosensor vent 137*b* via a conduit 135*b*; the second flow path, which also begins at the manifold 640, includes in series, the whole blood spectroscopic inlet transition chamber 614*a*, the whole blood optical chamber 616*a*, the whole blood spectroscopic overflow chamber 618*a*, the flow-through filtration chamber 634 (for extracting plasma from the whole blood using the hollow fiber filter bundle 660*a* with closed flange 682 shown; details of 660*a* are shown collectively in FIGS. 2A-2G), the filtration chamber outflow 620*a*, the filtration chamber capillary break 622*a*, and terminating at the filtration chamber vent 137*a* via conduit 135*a*. Also shown in the second flow path is the spectroscopic overflow chamber 618*a* overlapping with the filtration chamber 634. A third flow path, defined as the plasma flow path, begins at the plasma collection chamber 636, and includes in series the plasma biosensor chamber 672, the plasma spectroscopic inlet transition chamber 614*b*, the plasma optical chamber 616*b*, the plasma spectroscopic overflow chamber 618*b*, the plasma capillary break 622*c*, and terminating at the plasma vent 137*c* via a conduit 135*c*. A conduit 637 is also shown making fluid connection between the plasma biosensor chamber 672 and the plasma spectroscopic inlet transition chamber 614*b*. Those skilled in the art will appreciate that the conduit 637 can be considered to be a part of the plasma biosensor chamber 672. One plasma biosensor is shown as 652*c*, which is electrically connected through a medium or electrical conductor 676*c* to the biosensor electrical output contact 654*c*. Two whole blood biosensors are shown as 652*a* and 652*b*, which are connected to their respective biosensor electrical output contacts 654*a* and 654*b*, through respective electrical conductors 676*a* and 676*b*. In this embodiment of the apparatus, the force from a syringe plunger, or the force from blood in a vessel, is essential for blood flow from the inlet opening 612 towards the blood vents 137*a* and 137*b*, and plasma filtration from the filtration chamber 634 towards the plasma vent 137*c*. Capillary action is essential for plasma flow in the plasma flow path. The capillary break 622*c* prevents plasma from flowing out of the vent 137*c*; capillary breaks 622*a* and 622*b* function as buffer chambers for collecting excess blood injected into the apparatus 600*d*.

Referring collectively to FIGS. 7A-7C, shown are schematic drawings illustrating details of an apparatus 600*e* that is suitable for both extraction of plasma from a whole blood sample, and whole blood and plasma measurement according to a fifth embodiment of the invention.

Referring to FIG. 7A, shown is a schematic drawing illustrating a side view of an integrated needle and apparatus 600*e*, the hub of the needle 100 also comprising an apparatus 600*d*, similar to the apparatus identified as 600*d* and shown collectively in FIGS. 6A-6E.

FIG. 7B shows a cross-sectional view through the apparatus shown in FIG. 7A along line B-B, and showing parts already identified in FIG. 6E.

FIG. 7C is a perspective view of the integrated needle and apparatus 600*d* shown in FIG. 7A. Details of the apparatus 600*d* are already provided collectively with reference to FIGS. 6A-6E, and further details of the needle 100, showing the sharp open end 147, are provided collectively in FIGS. 8A-8F and FIGS. 10A-10F. Details of the hollow fiber filter bundle identified as 660*a* are not shown. The integrated needle and apparatus eliminates the need for a traditional syringe.

Referring collectively to FIGS. 8A-8F, shown are schematic drawings illustrating details of a needle 100 that can be used with the apparatus 600*d* illustrated collectively in FIGS. 6A-6E.

Referring to FIG. 8A, shown is a top view of the needle 100; FIG. 8B shows a left side view of the needle 100 shown in FIG. 8A; FIG. 8C shows a right side view of the needle shown in FIG. 8A; FIG. 8D shows a cross-sectional view through the needle 100 shown in FIG. 8A along line D-D; FIG. 8E shows a perspective view of the needle 100; and FIG. 8F shows an alternative perspective view of the needle 100. Those skilled in the art will appreciate that other suitable mating ends between needle and apparatus can be used, for example without limitations, threaded mating ends, and Luer lock mechanisms.

Still referring to FIGS. 8A-8F, the needle 100 comprises a shaft 143 and a hub with a front end 139 and a back end 140. It should be understood that the front end refers to a general area of the hub, and does not specifically identify any point or local area. Similarly, it should be understood that the back end refers to a general area of the hub, and does not specifically identify any point or local area. The shaft 143 has a sharp open end 147 and a second end, which is mounted in the passage 145 of the hub at the front end 140. The sharp open end 147 is usually the beveled end of the shaft, which is usually a hollow metal tube. The hollow portion of the shaft 143 is also referred to as the lumen (not shown). The bevel provides a point for piercing a blood vessel. Also shown collectively in FIG. 8A and FIG. 8F is the central axis 133*a*, which runs through the center of the shaft 143, along its length. The section of the shaft 143 mounted inside the hub is not shown. The passage 145 of the hub is fluidly connected to the lumen of the shaft, and a flow path is defined by the sharp open end 147, which leads into the lumen of the shaft 143, which leads into the passage 145 of the hub, and terminates at a blunt open end 137 of the hub. The blunt open end 137 is located at the back end 140 of the hub. The front end of the hub 139 contains external threads 173 for mating with complementary internal threads 175 in a barrel 200 illustrated collectively in FIGS. 9A-9F, and the blunt open end 137 is housed in a tapered projection 171, which resembles the male end of a syringe.

Referring collectively to FIGS. 9A-9F, shown are schematic drawings illustrating details of a barrel 200 for sheathing and unsheathing the needle 100 illustrated collectively in FIGS. 8A-8F.

Referring to FIG. 9A, shown is a top view of the barrel 200; FIG. 9B shows a left side view of the barrel 200 shown in FIG. 9A; FIG. 9C shows a cross-sectional view through the barrel 200 shown in FIG. 9A along line C-C; FIG. 9D shows a right side view of the barrel 200 shown in FIG. 9A; FIG. 9E shows an alternative cross-sectional view through the barrel 200 shown in FIG. 9A along line E-E; and FIG. 9F shows a perspective view of the barrel 200.

Also illustrated collectively in FIGS. 9A-9F is: an opening 167 in the open anterior end 159 of the barrel 200, for movement of the needle shaft 143; an opening 165 in the open posterior end 161 of the barrel 200, for movement of the back end 140 of the needle hub shown in FIGS. 8A, E & F; and an axis 133*b* which runs through the center of the barrel, along the length of the barrel. The barrel 200 comprises an internal chamber 153 for housing the front end 139 of the hub shown in FIG. 8. The central axis 133*a* of the needle 100 and axis 133*b* of the barrel 200 are shown to be coaxial (illustrated in FIG. 10A), but the axes could also be parallel without being coaxial for example, if the outer design of the barrel is not cylindrical. Also shown collectively in FIGS. 9A-9F are internal threads 175 for mating with the external threads 173 in the hub of the needle 100. In this particular embodiment of the barrel 200, the threads 175 do not run continuously throughout the length of the barrel, and prevents the front end 139 of the needle hub from moving beyond the threaded area in the barrel 200.

Referring collectively to FIGS. 10A-10F, shown are schematic drawings illustrating details of a needle (100) and barrel (200) assembly 300 with the needle shaft 143 retracted into the barrel 200.

Referring to FIG. 10A, shown is a top view of the needle and barrel assembly 300; FIG. 10B shows a left side view of the assembly 300 shown in FIG. 10A; FIG. 10C shows a right side view of the assembly 300 shown in FIG. 10A; FIG. 10D shows a cross-sectional view through the assembly 300 shown in FIG. 10A along line D-D; FIG. 10E shows a perspective view of the assembly 300; and FIG. 10F shows an alternative perspective view of the assembly 300. The assembly 300 illustrated collectively in FIGS. 10A-10F is an assembly of the needle 100 illustrated collectively in FIGS. 8A-8F, and the barrel 200 illustrated collectively in FIGS. 9A-9F, and accordingly, elements common to these share common reference numerals.

Referring collectively to FIGS. 11A-11C, shown are schematic drawings illustrating details of an apparatus 600*f* that is suitable for both extraction of plasma from a whole blood sample, and whole blood and plasma measurement according to a sixth embodiment of the invention.

Referring to FIG. 11A, shown is a top view of the apparatus 600*f*; FIG. 11B is a first cross-sectional view through the apparatus 600*f* shown in FIG. 11A along line B-B, and FIG. 11C is a second cross-sectional view through the apparatus 600*f* shown in FIG. 11B along line C-C. The apparatus 600*f* illustrated collectively in FIGS. 11A-11C is similar to the apparatus illustrated collectively in FIGS. 6A-6E, and accordingly, elements common to them share common reference numerals. The first difference is that apparatus 600*f* does not have an inlet opening 612 in an inlet chamber 670 that is designed to accommodate the male end of a syringe. Instead, the inlet opening 612 shown collectively in FIGS. 11A and 11C is the opening in a piece of capillary tubing 672. The second difference is that the three flow paths terminate in a single suction chamber 960*d*. The third difference is that the distances A and B shown in FIG. 11A are about equal. A meter used to read this apparatus could have a single EMR path or two EMR paths. The apparatus 600*d* illustrated collectively in FIGS. 6A-6E requires two EMR paths: one for the whole blood optical chamber 616*a*, and another for the plasma optical chamber 616*b*, because the optical chambers are not located approximately equidistant from their respective sides of the apparatus 600*d*, shown as distances A and B in FIG. 11A. The apparatus illustrated collectively in FIGS. 11A-11C could operate with either a single EMR path or two EMR paths, since the distance A is about equal to the distance B (FIG. 11A).

When the apparatus 600*f* containing sample is inserted into a slot of a meter that provides a single EMR path, the biosensor measurement and one spectroscopic measurement is performed. The spectroscopic measurement is performed either on the blood or on the plasma. In order to perform the second spectroscopic measurement, the apparatus 600*f* must be removed and flipped over 180 degrees before reinsertion in the apparatus 600*f*. In an embodiment of a joint-diagnostic spectroscopic and biosensor meter, the software allows the meter to detect whether the sample in the EMR path is plasma or whole blood, and the appropriate spectroscopic algorithm is applied. It must also be noted that the biosensor electrical output contact is not affected after flipping the apparatus 600*f*, due to the location of the contacts, and the biosensor measurements are preferably performed during the first insertion of the apparatus 600*f*.

Referring collectively to FIGS. 12A-12D, shown are schematic drawings illustrating details of an example of a joint-diagnostic spectroscopic and biosensor meter 900, required for sample measurement in the apparatus described. In this embodiment of the meter, there is no aperture for channeling the EMR from the EMR source 880 to the sample, and there is a lens 870 for focusing EMR emerging from the sample, unto the photodetector included in part 890.

Referring to FIG. 12A, shown is a front view of the joint-diagnostic spectroscopic and biosensor meter 900; FIG. 12B is a first cross-sectional view through the joint-diagnostic spectroscopic and biosensor meter 900 shown in FIG. 12A along line B-B, showing the slot 800 as an integral part of the housing 892 of the meter 900; FIG. 12C is a second cross-sectional view through the joint-diagnostic spectroscopic and biosensor meter 900 shown in FIG. 12A along line C-C; and FIG. 12D is a perspective view of the joint-diagnostic spectroscopic and biosensor meter 900, showing the housing 892, a display screen 894, and three buttons 882*a*, 882*b* and 882*c*, for manipulating the display functions. The meter slot 800 illustrated collectively in FIGS. 12A-12D is similar to the meter slot 800 illustrated collectively in FIGS. 13A-13C, and accordingly, elements common to them share common reference numerals. The meter slot is designed to accept some embodiments of the present invention.

Referring collectively to FIGS. 13A-13C, shown are schematic drawings illustrating details of the meter slot 800, for a joint-diagnostic spectroscopic and biosensor meter.

Referring to FIG. 13A, shown is a front view of the meter slot 800; FIG. 13B is a cross-sectional view through the apparatus slot 800 shown in FIG. 13A along line B-B; and FIG. 13C is a perspective view of the meter slot 800. Shown in the slot 800 are two electrical input contacts 854*a* and 854*b*, with passages 876*a* and 876*b* respectively, for making electrical connections between the contacts 854*a* and 854*b* with the meter processor. Also shown are notches 812*a* and 812*b* for correct insertion of the apparatus. The apparatus (not shown) for which the slot 800 is designed has ridges than fit in the notches 812*a* and 812*b*.

Referring collectively to FIGS. 14A-14E, shown are schematic drawings illustrating details of an apparatus 600*g* that is suitable for both extraction of plasma from a whole blood sample, and plasma measurement according to a seventh embodiment of the invention.

Figure 14D:
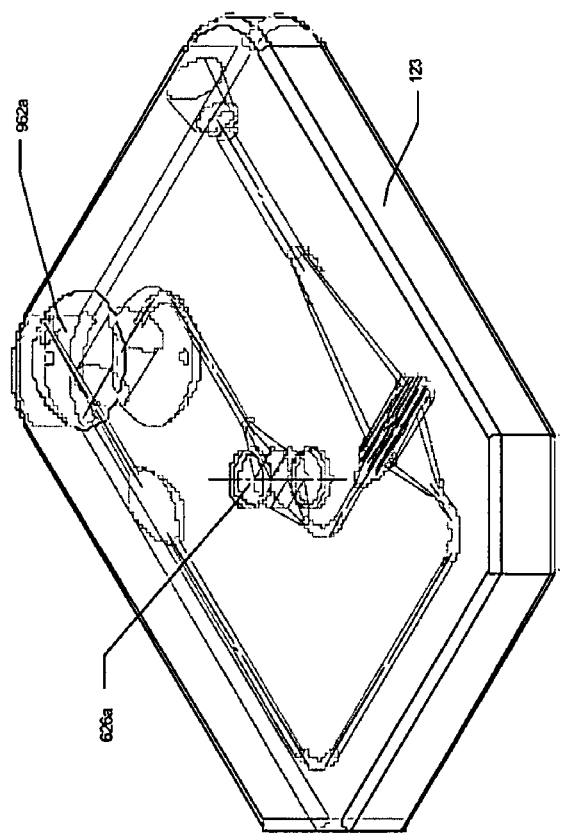
FIG. 14D is a perspective view of the apparatus 600g shown in FIG. 14A.
Figure 14E:
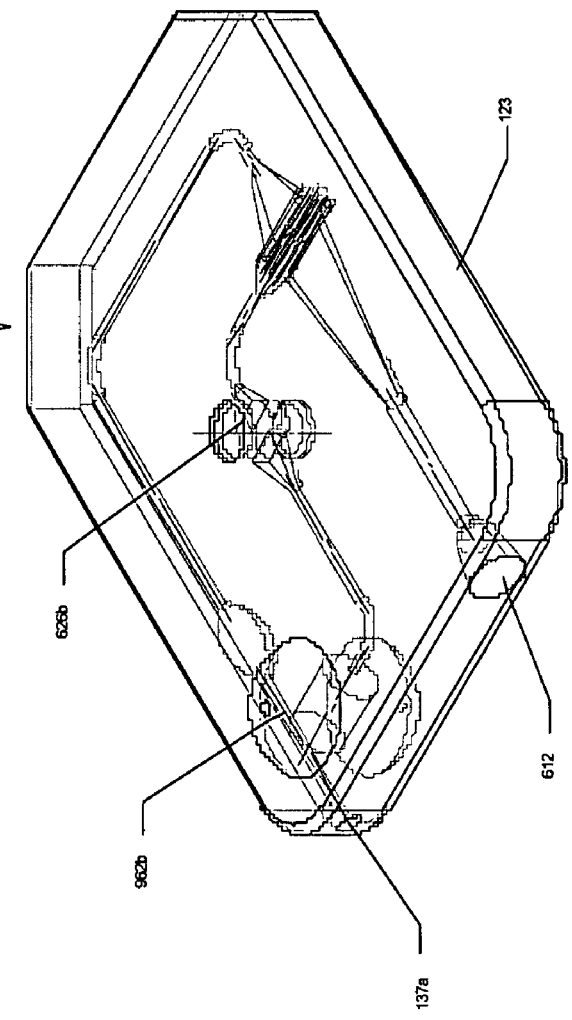
FIG. 14E is an alternative perspective view of the apparatus 600g shown in FIG. 14A.

Referring to FIG. 14A, shown is a top view of the apparatus 600*g*; FIG. 14B is a first cross-sectional view through the apparatus 600*g* shown in FIG. 14A along line B-B, and FIG. 14C is a second cross-sectional view through the apparatus 600*g* shown in FIG. 14B along line C-C; FIG. 14D is a perspective view of the apparatus 600*g*; and FIG. 14E is an alternative perspective view of the apparatus 600*g*. The apparatus 600*g* illustrated collectively in FIGS. 14A-14E is similar to the apparatus illustrated collectively in FIGS. 3A-3F, and accordingly, elements common to them share common reference numerals. The first difference is that the filtration chamber comprises a hollow fiber filter bundle 660*a*, illustrated in details collectively in FIGS. 2A-2G. The second difference is the inlet opening 612 is housed in a flared inlet chamber 670, instead of a piece of capillary tubing.

In a first method of use, the suction chamber 960*c* is squeezed to dispel air, and then the male end of a syringe containing blood is inserted into the inlet chamber 670. Before releasing the suction chamber, blood is slowly injected into the apparatus 600g until it passes the filter 660a. The suction chamber is then released while blood is still injected slowly into the apparatus. Those skilled in the art will appreciate that the sizes of the internal chambers could be optimized so that the plasma optical chamber 616b is full by the time the blood arrives at the capillary break 622a. In this embodiment, the capillary break functions as a buffer chamber for excess blood, to prevent any blood from escaping through the vent 137a. The apparatus 600g is constructed with material that allows the user to see the blood and plasma in their respective flow paths. In some embodiments, the apparatus includes at least one visible guide line, preferably after the filter, to indicate when the suction chamber must be released.

In a second method of use, the skin of the patient is pricked with a lancet (also referred to as a pin prick), and a blood drop is allowed to form on the skin. After the suction chamber 960c is squeezed to dispel air, the inlet opening 612 of the apparatus 600g is placed over the drop of blood, and blood is gently squeezed into the apparatus, as if blood was injected into the apparatus from a syringe. The suction chamber 960c is then released, and blood is allowed to flow into the blood flow path. The procedure will have to be repeated if blood flow is insufficient. Preferably, the site of the pin prick is warmed with a mild heating pad for a few minutes, before the skin is pricked again. Warming the skin promotes blood flow.

Referring collectively to FIGS. 15A-15E, shown are schematic drawings illustrating details of a combined apparatus (600h) and cap (960) 600k, suitable for both extraction of plasma from a whole blood sample, and plasma measurement according to an eight embodiment of the invention.

FIG. 15A is a schematic drawing showing details of the top view of combined apparatus and cap 600k; FIG. 15B is a first cross-sectional view through the combined apparatus and cap 600k shown in FIG. 15A along line B-B; FIG. 15C is a second cross-sectional view through the combined apparatus and cap 600k shown in FIG. 15B along line C-C; FIG. 15D is a perspective view of the combined apparatus and cap 600k; and FIG. 15E is an alternative perspective view of the combined apparatus and cap 600k.

Apparatus 600h illustrated collectively in FIGS. 15A-15E is similar to the apparatus illustrated collectively in FIGS. 4A-4D, and accordingly, elements common to them share common reference numerals. The first difference is that the filtration chamber comprises a hollow fiber filter bundle 660a, illustrated in details collectively in FIGS. 2A-2G. The second difference is that the inlet opening 612 is housed in an extended piece of capillary tubing.

The extended capillary tubing is particularly useful for reaching into a microtube containing anticoagulated blood, for bilirubin measurement, which is useful for diagnosis and for monitoring treatment of neonatal jaundice. In use, with the suction chamber is squeezed to dispel air, the inlet opening 612 is submerged into the anticoagulated blood in the microtube. Keeping the inlet opening 612 submerged in the blood, the suction chamber is released, drawing blood into the blood flow path, and subsequently drawing plasma into the plasma flow path. Those skilled in the art will appreciate that the rebound in the flexible members 962a and 962b, the relative sizes of the suction chambers 960a and 960b, and the sizes of the different sections of the flow paths could be optimized for efficient blood flow and plasma filtration.

Since the only opening in the apparatus 600h is the inlet opening 612, the cap 960 is useful to prevent blood contamination. This non limiting example of a cap comprises a tether 964 and a retaining ring 966 for keeping the cap attached to the apparatus 600h.

Those skilled in the art will appreciate that the housing of the apparatus described can be manufactured in two halves, a top half and a bottom half, and they could be assembled together by glue or ultrasonic welding. For clarity, FIG. 14D is a perspective view of the top half of apparatus 600g, and FIG. 14E is a perspective view of the bottom half of apparatus 600g. Those skilled in the art will also appreciate that the hollow fiber filter bundle 660a shown in FIG. 14C, can be made separately and sandwiched between the two halves during assembly, so that the housing fits tightly around the flanges 682 and 684 (FIGS. 2E & 2G), sealing the flanges at their periphery, and maintaining a barrier between the blood compartment and the plasma compartment.

While the above description provides example embodiments, it will be appreciated that the present invention is susceptible to modification and change without departing from the fair meaning and scope of the accompanying claims. Accordingly, what has been described is merely illustrative of the application of aspects of embodiments of the invention. Numerous modifications and variations of the present invention are possible in light of the above teachings. It is therefore to be understood that within the scope of the appended claims, the invention may be practiced otherwise than as specifically described herein. Furthermore, the discussed combination of features might not be absolutely necessary for the inventive solution.

The invention claimed is:

1. A disposable apparatus adapted for insertion into the slot of a meter for measuring at least one plasma analyte in plasma extracted from a blood sample within the apparatus, the apparatus comprising:
   a housing;
   an inlet opening in the housing for receiving the blood sample;
   a first groove in the housing defining a blood flow path beginning at the inlet opening and terminating at a manually operable first compression suction chamber for facilitating blood flow in the blood flow path, wherein the first compression suction chamber comprises a first cavity within the housing, wherein a wall portion of the first cavity is defined by the housing;
   a filtration chamber comprising a membrane separating a plasma compartment from the blood flow path, wherein the blood flow path fluidly intersects with the filtration chamber, and a blood flow direction defined by the blood flow path at the intersection with the filtration chamber is substantially parallel to a surface of the membrane; and
   a second groove in the housing defining a plasma flow path beginning at the plasma compartment and terminating at a manually operable second compression suction chamber for pulling the plasma across the membrane from the blood flow path into the plasma flow path, wherein the second compression suction chamber comprises a second cavity within the housing, wherein a wall portion of the second cavity is defined by the housing, and wherein the plasma flow path comprises at least one of:
   an optical chamber defining a void for containing the plasma for analysis,
   wherein the optical chamber comprises at least one optical wall-portion to facilitate detection of an EMR-based signal derived from the plasma for measuring the at least one plasma analyte, and a plasma biosensor chamber comprising at least one biosensor for measuring the at least one plasma analyte, wherein the at least one biosensor is in electrical communication with an electrical output located on an external surface of the housing, the electrical output being operable to receive plasma biosensor data from the biosensor and to transmit the biosensor data to the meter when the apparatus is inserted in the slot.

2. The disposable apparatus according to claim 1, wherein the blood flow path further comprises a blood analyte signal providing means in the blood flow path for providing a signal to the meter for measuring at least one blood analyte.

3. The disposable apparatus according to claim 1, wherein the optical chamber comprises two optical chamber wall-portions for performing spectroscopic measurement on the plasma, wherein the average internal distance between the two optical chamber wall-portions is in an approximate range of 0.02 mm to 5 mm.

4. The disposable apparatus according to claim 3, further comprising a reflective coating on one of the optical chamber wall-portions.

5. The disposable apparatus according to claim 1, wherein the plasma flow path further comprises a reagent.

6. The disposable apparatus according to claim 1, wherein the blood flow path includes an anticoagulant.

7. The disposable apparatus according to claim 1, wherein the blood flow path terminates at the first compression suction chamber, and the plasma flow path terminates at a the second compression suction chamber, and wherein the second compression suction chamber is not fluidly connected to the first compression suction chamber such that the first compression suction chamber and the second compression suction chamber are operable to generate different pressures in the blood flow path and the plasma flow path.

8. The disposable apparatus according to claim 1, further comprising at least one visible guide line for indicating a compression level for the compression suction chamber.

9. The disposable apparatus according to claim 1, further comprising a barcode containing at least information regarding calibration for measurement of an analyte.

10. The disposable apparatus according to claim 1, wherein the biosensor comprises a transducer for converting at least one property of the plasma into an electrical signal.

11. The disposable apparatus according to claim 10, wherein the transducer comprises at least one active surface for contacting the fluid.

12. The disposable apparatus according to claim 11, wherein the at least one active surface is one of a chemical sensitive surface and an ionic sensitive surface.

13. A disposable apparatus according to claim 1, wherein the at least one biosensor comprises at least one of a transistor, an ion-selective membrane, a membrane-bound enzyme, a membrane-bound antigen, a membrane-bound antibody and a membrane-bound strand of nucleic acid.

14. The disposable apparatus according to claim 1, wherein the membrane is in the form of a hollow fiber filter, and the filtration chamber comprises at least one hollow fiber filter.

15. The disposable apparatus according to claim 14, wherein at the fluid intersection of the blood flow path and the filtration chamber, the direction of blood flow defined by the blood flow path is substantially parallel to the longitudinal axis of the at least one hollow fiber filter.

16. The disposable apparatus according to claim 1, wherein at least one of the manually operable first compression suction chamber and the manually operable second compression chamber comprise a first member and a second member, the first or second cavity extends between the first member and the second member, the first member is flexible and is located substantially opposite the second member, the first member is manually squeezable to move toward the second member, and after being moved toward the second member the first member is resiliently biased to move away from the second member to generate a negative pressure in the blood flow path or the plasma flow path to facilitate blood flow or plasma flow, respectively.

17. The disposable apparatus according to claim 16, wherein the first member is manually squeezable to move toward the second member by a force applied by a portion of a human hand.

18. The disposable apparatus according to claim 16, wherein the first member is manually squeezable to move toward the second member by a force applied by a single finger.

19. A disposable apparatus adapted for insertion into the slot of a meter for measuring at least one plasma analyte in plasma extracted from a blood sample within the apparatus, the apparatus comprising:
a housing;
an inlet opening in the housing for receiving the blood sample;
a first groove in the housing defining a blood flow path beginning at the inlet opening and terminating at a vent for facilitating blood flow in the blood flow path;
a filtration chamber comprising a membrane separating a plasma compartment from the blood flow path, wherein the blood flow path fluidly intersects with the filtration chamber; and,
a second groove in the housing defining a plasma flow path beginning at the plasma compartment and terminating at a manually operable compression suction chamber for pulling the plasma across the membrane from the blood flow path into the plasma flow path, wherein the manually operable compression suction chamber comprises a cavity within the housing, wherein a wall portion of the cavity is defined by the housing, and wherein the plasma flow path comprises at least one of:
an optical chamber defining a void for containing the plasma for analysis, wherein the optical chamber comprises at least one optical wall-portion to facilitate detection of an EMR-based signal derived from the plasma for measuring the at least one plasma analyte, and a plasma biosensor chamber comprising at least one biosensor for measuring the at least one plasma analyte, wherein the at least one biosensor is in electrical communication with an electrical output located on an external surface of the housing, the electrical output being operable to receive plasma biosensor data from the biosensor and to transmit the biosensor data to the meter when the apparatus is inserted in the slot.

20. The disposable apparatus according to claim 19, wherein
the manually operable compression suction chamber comprises a first member and a second member, the cavity extends between the first member and the second member, the first member is flexible and is located substantially opposite the second member, the first member is manually squeezable to move toward the second member, and after being moved toward the second member the first member is resiliently biased to move away from the second member to generate a negative pressure in the plasma flow path to facilitate plasma flow.

* * * * *

UNITED STATES PATENT AND TRADEMARK OFFICE
CERTIFICATE OF CORRECTION

| | | |
|---|---|---|
| PATENT NO. | : 7,816,124 B2 | |
| APPLICATION NO. | : 11/432616 | |
| DATED | : October 19, 2010 | |
| INVENTOR(S) | : James Samsoondar | |

It is certified that error appears in the above-identified patent and that said Letters Patent is hereby corrected as shown below:

Column 23, line 26, "a the" should read --the--.

Signed and Sealed this
Twenty-eighth Day of December, 2010

David J. Kappos
*Director of the United States Patent and Trademark Office*